United States Patent
Leeson et al.

[11] Patent Number: 5,700,809
[45] Date of Patent: Dec. 23, 1997

[54] PYRROLO-PYRIDINE DERIVATIVES

[75] Inventors: Paul David Leeson, Cambridge; Adrian Leonard Smith, Bishops Stortford; Mark Peter Ridgill, Watton-At-Stone; Raymond Baker, Green Tye; Neil Roy Curtis, Puckeridge; Janusz Jozef Kulagowski, Bishops Stortford, all of Great Britain

[73] Assignee: Merck Sharp & Dohme, Ltd., Hoddesdon, England

[21] Appl. No.: 513,828

[22] PCT Filed: Feb. 25, 1994

[86] PCT No.: PCT/GB94/00384

§ 371 Date: Aug. 29, 1995

§ 102(e) Date: Aug. 29, 1995

[87] PCT Pub. No.: WO94/20459

PCT Pub. Date: Sep. 15, 1994

[30] Foreign Application Priority Data

Mar. 1, 1993 [GB] United Kingdom .................. 9304110
Aug. 5, 1993 [GB] United Kingdom .................. 9316260

[51] Int. Cl.⁶ ............... C07D 410/14; C07D 109/14; C07D 217/24; A61K 31/54
[52] U.S. Cl. ............... 514/300; 546/113
[58] Field of Search ............... 514/300; 546/113

[56] References Cited

U.S. PATENT DOCUMENTS

| | | | |
|---|---|---|---|
| 5,124,335 | 6/1992 | Patchettet et al. | 514/300 |
| 5,432,177 | 7/1995 | Baker et al. | 514/253 |
| 5,563,150 | 10/1996 | Curtis et al. | 514/300 |
| 5,563,152 | 10/1996 | Kulagowski et al. | 514/300 |
| 5,576,319 | 11/1996 | Baker et al. | 514/253 |
| 5,622,950 | 4/1997 | Baker et al. | 514/249 |

FOREIGN PATENT DOCUMENTS

| | | |
|---|---|---|
| 2 044 254 | 1/1980 | United Kingdom . |
| 2044254 | 10/1980 | United Kingdom . |
| 9605200 | 2/1996 | WIPO . |

OTHER PUBLICATIONS

R. Herbert et al., Syntheses and Properties of 1–H–Pyrrolo–[2,3–b]–Pyridines, *J. Chem. Soc.(c)*, (1969), 1505–1514.
H. Bottcher et al., Synthesis and Dopaminergic Activity of Some 3–(1,2,3,6–Tetrahydro–1–Pyridylalkly) Indoles, A Novel Conformational Model to Explain Structure–Activity Relationships *J. Med. Chem.* 1992, 35, 4020–2026.

*Primary Examiner*—Mukund J. Shah
*Assistant Examiner*—Tamthom T. Ngo
*Attorney, Agent, or Firm*—Robert J. North; Melvin Winokur

[57] ABSTRACT

Compounds of formula I are ligands for dopamine receptor subtypes within the body and are therefore useful in the treatment and/or prevention of disorders of the dopamine system, in particular schizophrenia.

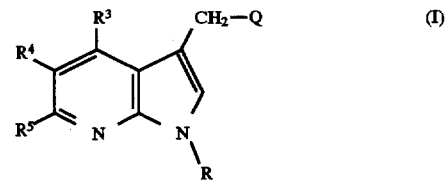

wherein Q is

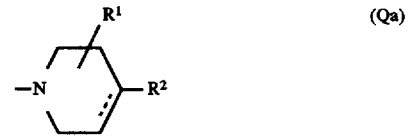

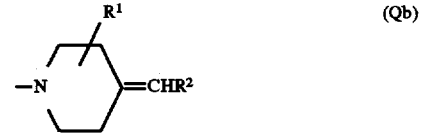

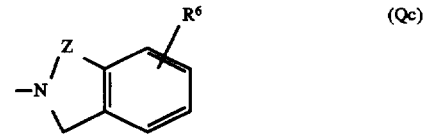

9 Claims, No Drawings

PYRROLO-PYRIDINE DERIVATIVES

This invention relates to a particular class of heteroaromatic compounds. More particularly, the invention is concerned with substituted pyrrolo[2,3-b]-pyridine derivatives which are ligands for dopamine receptor subtypes within the body and are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

The disclosure of GB-A-2044254 generically encompasses inter alia a class of 3-[piperidin-1-ylalkyl]-1H-pyrrolo[2,3-b]pyridine derivatives substituted on the piperidine ring by an isoindoledione or like moiety. These compounds are alleged therein to be useful as antidepressants. There is, however, no specific disclosure in GB-A-2044254 of a substituted pyrrolo[2,3-b]pyridine derivative, nor indeed any suggestion that such compounds would be of benefit in the treatment and/or prevention of disorders of the dopamine system.

The compounds in accordance with the present invention, being ligands for dopamine receptor subtypes within the body, are accordingly of use in the treatment and/or prevention of disorders of the dopamine system.

The present invention accordingly provides a compound of formula I, or a salt or prodrug thereof:

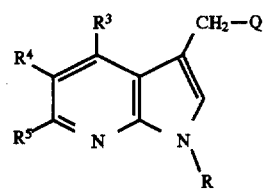

wherein

R represents hydrogen or $C_{1-6}$ alkyl;

Q represents a moiety of formula Qa, Qb or Qc:

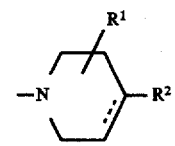

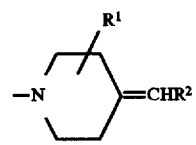

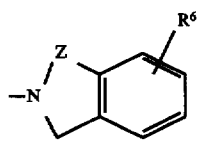

in which the broken line represents an optional chemical bond;

$R^1$ represents hydrogen, or an optionally substituted $C_{1-6}$ alkyl, $C_{1-6}$ alkoxy, $C_{1-6}$ alkenyl, $C_{1-6}$ alkynyl, aryl, aryl($C_{1-6}$)alkyl, aryl($C_{1-6}$)alkoxy, aryl($C_{1-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$) alkenyl or heteroaryl($C_{2-6}$)alkynyl group;

$R^2$ represents an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryloxy($C_{1-6}$)alkyl, aryl($C_{1-6}$)alkoxy, aryl($C_{2-6}$) alkenyl, aryl($C_{2-6}$)alkynyl, $C_{3-7}$ heterocycloalkyl($C_{1-6}$) alkyl, heteroaryl, heteroaryl($C_{1-6}$)alkyl, heteroaryl ($C_{2-6}$) alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$;

Z represents —$CH_2$— or —$CH_2CH_2$—;

$R^6$ represents hydrogen or halogen, or an optionally substituted $C_{1-6}$ alkyl, $C_{1-6}$ alkoxy, aryl, aryloxy, aryl ($C_{1-6}$)alkyl, aryl($C_{1-6}$)alkoxy or heteroaryl group; and $R^a$ and $R^b$ independently represent hydrogen, hydrocarbon or a heterocyclic group.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents R, $R^1$, $R^2$ and $R^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$, $R^2$ and $R^6$ include phenyl and naphthyl.

Particular aryl($C_{1-6}$)alkyl groups within the scope of the term "hydrocarbon" and within the definition of the substituents $R^1$, $R^2$ and $R^6$ include benzyl, naphthylmethyl, phenethyl and phenylpropyl.

A particular aryl($C_{2-6}$)alkenyl group within the scope of the term "hydrocarbon" and within the definition of the substituents $R^1$ and $R^2$ is phenylethenyl.

A particular aryl($C_{2-6}$)alkynyl group within the scope of the term "hydrocarbon" and within the definition of the substituents $R^1$ and $R^2$ is phenylethynyl.

Suitable heterocycloalkyl groups include azetidinyl, pyrrolidyl, piperidyl, piperazinyl, morpholinyl and tetrahydrofuryl groups.

A particular $C_{3-7}$ heterocycloalkyl($C_{1-6}$)alkyl group within the scope of the expression "a heterocyclic group" and within the definition of the substituents $R^1$ and $R^2$ is tetrahydrofurylethyl.

Suitable heteroaryl groups within the scope of the expression "a heterocyclic group" and within the definition of the substituents $R^1$, $R^2$ and $R^6$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl($C_{1-6}$)alkyl groups within the scope of the expression "a heterocyclic group" and within the definition of the substituents $R^1$ and $R^2$ include thienylmethyl, pyridylmethyl, pyrimidinylmethyl, pyrazinylmethyl and furylmethyl.

Particular heteroaryl($C_{2-6}$)alkenyl groups within the scope of the term "hydrocarbon" and within the definition of the substituents $R^1$ and $R^2$ include furylethenyl and thienylethenyl.

The hydrocarbon and heterocyclic groups, as well as the substituents $R^1$, $R^2$ and $R^6$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyloxy, —NR′R″, —NR″COR‴, —NR″CO₂R‴, —NR″SO₂R‴, —CH₂NR″SO₂R‴, —NHCONR′R″, —PO(OR′)(OR″), —CONR′R″, —SO₂NR′R″ and —CH₂SO₂NR′R″, in which R′ and R″ independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof are encompassed within the scope of the present invention.

Suitably, the substituent R represents hydrogen or methyl, especially hydrogen.

Suitably, the substituent $R^1$ represents hydrogen.

Suitable values for the substituent $R^2$ include $C_{1-6}$ alkyl, aryl, aryl($C_{1-6}$)alkyl, aryloxy($C_{1-6}$)alkyl, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl or heteroaryl($C_{2-6}$)alkenyl, any of which groups may be optionally substituted. Examples of optional substituents on the group $R^2$ include $C_{1-6}$ alkyl, halogen, nitro, $C_{1-6}$ alkoxy, aryloxy and arylcarbonyloxy.

Particular values of $R^2$ include methyl, benzoyloxymethyl, ethyl, n-propyl, isopropyl, phenyl, chlorophenyl, ethylphenyl, methoxyphenyl, nitrophenyl, naphthyl, benzyl, chlorobenzyl, phenethyl, phenoxymethyl, phenylethenyl, chloro-phenylethenyl, methoxy-phenylethenyl, phenylethynyl, tetrahydrofuryl-ethyl, indolyl, benzofuryl, benzthienyl, furylethyl, methyl-furylethyl, thienylethenyl and methyl-furylethenyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy.

Particular values of $R^6$ include hydrogen, methoxy, phenyl, chlorophenyl, phenoxy, benzyloxy, thienyl, chloro and bromo.

One sub-class of compounds according to the invention is represented by the compounds of formula IIA, and salts and prodrugs thereof:

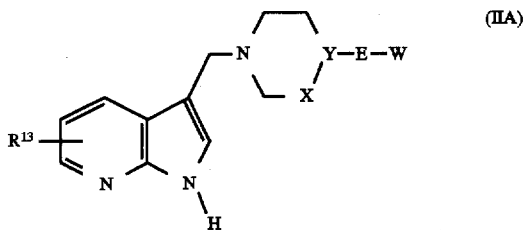
(IIA)

wherein

E represents —(CH$_2$)$_n$—, —CH=CH— or —C≡C—;
n is zero, 1, 2 or 3;
—X—Y— represents —CH$_2$—CH— or —CH=C—;
W represents a group of formula (i), (ii), (iii), (iv), (v) or (vi):

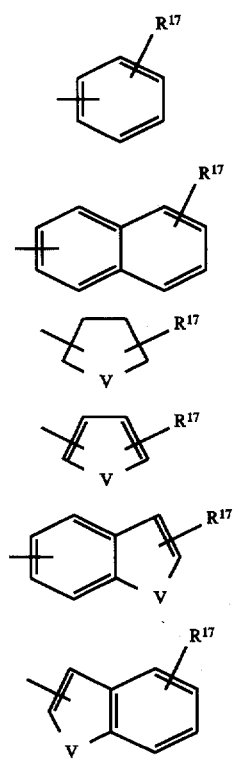

in which V represents oxygen, sulphur or NH; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl.

Particular values of $R^{13}$ include hydrogen, fluoro, chloro, methyl, ethyl, methoxy and benzyloxy.

Particular values of $R^{17}$ include hydrogen, chloro, methyl, methoxy and nitro.

A particular subset of the compounds of formula IIA as defined above is represented by the compounds of formula IIB, and salts and prodrugs thereof:

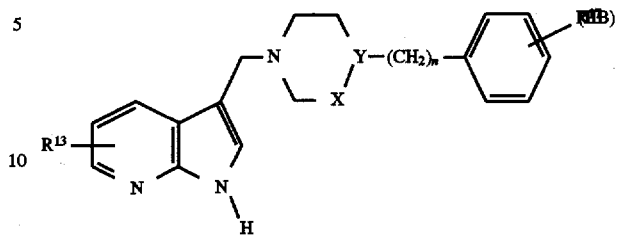
(IIB)

wherein n, X, Y, $R^{13}$ and $R^{17}$ are as defined with reference to formula IIA above.

Another sub-class of compounds according to the invention is represented by the compounds of formula IIC, and salts and prodrugs thereof:

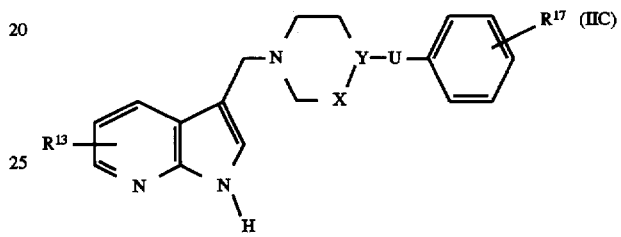
(IIC)

wherein

U represents —CH=CH—, —C≡C— or —CH$_2$O—; and
X, Y, $R^{13}$ and $R^{17}$ are as defined with reference to formula IIA above.

A particular subset of the compounds of formula IIC as defined above comprises those compounds wherein U represents —CH=CH—, in particular in the (E) configuration.

A further sub-class of compounds according to the invention is represented by the compounds of formula IID, and salts and prodrugs thereof:

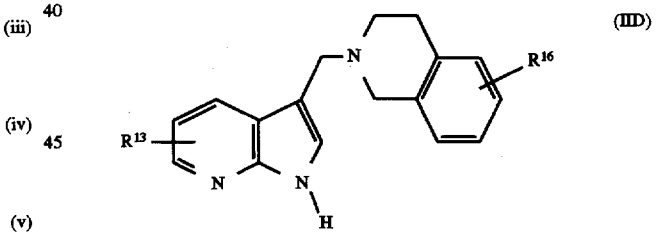
(IID)

wherein $R^{13}$ is as defined with reference to formula IIA above; and
$R^{16}$ represents hydrogen, halogen, $C_{1-6}$ alkyl, $C_{1-6}$ alkoxy, aryl, halo-aryl, aryloxy, aryl($C_{1-6}$)alkyl, aryl($C_{1-6}$) alkoxy or heteroaryl.

Particular values of $R^{16}$ include hydrogen, methoxy, phenyl, chlorophenyl, phenoxy, benzyloxy, thienyl, chloro and bromo.

Specific compounds within the scope of the present invention include:

3-(1,2,3,4-tetrahydroisoquinolin-2-yl)methyl-1H-pyrrolo[2,3-b]pyridine;

3-[4-(2-phenylethyl)piperidin-1-yl]methyl-1H-pyrrolo[2,3-b]pyridine;

3-(4-phenyl-1,2,3,6-tetrahydropyrid-1-yl)methyl-1H-pyrrolo[2,3-b]pyridine;

(E)-3-[4-(2-phenylethenyl)-1,2,3,6-tetrahydropyrid-1-yl]methyl-1H-pyrrolo[2,3-b]pyridine;

3-[4-(2-phenylethyl)-1,2,3,6-tetrahydropyrid-1-yl]methyl-1H-pyrrolo[2,3-b]pyridine;

3-[4-(naphth-2-yl)-1,2,3,6-tetrahydropyridin-1-yl]methyl-1H-pyrrolo[2,3-b]pyridine;

3-[4-(4-methoxyphenyl)-1,2,3,6-tetrahydropyridin-1-yl]methyl-1H-pyrrolo[2,3-b]pyridine;

3-[4-(1H-indol-5-yl)-1,2,3,6-tetrahydropyridin-1-yl]methyl-1H-pyrrolo[2,3-b]pyridine;

3-[4-(benzofuran-5-yl)-1,2,3,6-tetrahydropyridin-1-yl]methyl-1H-pyrrolo[2,3-b]pyridine;

3-[4-(benzofuran-6-yl)-1,2,3,6-tetrahydropyridin-1-yl]methyl-1H-pyrrolo[2,3-b]pyridine;

3-[4-(benzothiophen-2-yl)-1,2,3,6-tetrahydropyridin-1-yl]methyl-1H-pyrrolo[2,3-b]pyridine;

3-[4-(benzofuran-2-yl)-1,2,3,6-tetrahydropyridin-1-yl]methyl-1H-pyrrolo[2,3-b]pyridine;

3-[4-(2-phenylethynyl)-1,2,3,6-tetrahydropyridin-1-yl]methyl-1H-pyrrolo[2,3-b]pyridine;

(E)-3-[4-(2-(thiophen-3-yl)ethenyl)-1,2,3,6-tetrahydropyridin-1-yl]methyl-1H-pyrrolo[2,3-b]pyridine;

(E)-3-[4-(2-(2-chlorophenyl)ethenyl)-1,2,3,6-tetrahydropyridin-1-yl]methyl-1H-pyrrolo[2,3-b]pyridine;

(E)-3-[4-(2-(4-chlorophenyl)ethenyl)-1,2,3,6-tetrahydropyridin-1-yl]methyl-1H-pyrrolo[2,3-b]pyridine;

(E)-3-[4-(2-(thiophen-2-yl)ethenyl)-1,2,3,6-tetrahydropyridin-1-yl]methyl-1H-pyrrolo[2,3-b]pyridine;

3-[4-(2-(furan-2-yl)ethyl)-1,2,3,6-tetrahydropyridin-1-yl]methyl-1H-pyrrolo[2,3-b]pyridine;

3-[4-(2-(tetrahydrofuran-2-yl)ethyl)-1,2,3,6-tetrahydropyridin-1-yl]methyl-1H-pyrrolo[2,3-b]pyridine;

3-[4-(2-(5-methylfuran-2-yl)ethyl)-1,2,3,6-tetrahydropyridin-1-yl]methyl-1H-pyrrolo[2,3-b]pyridine;

3-(4-ethyl-1,2,3,6-tetrahydropyridin-1-yl)b methyl-1H-pyrrolo[2,3-b]pyridine;

3-(4-benzoyloxymethyl-1,2,3,6-tetrahydropyridin-1-yl)methyl-1H-pyrrolo[2,3-b]pyridine;

(E)-3-[4-(2-(3-methoxyphenyl)ethenyl)-1,2,3,6-tetrahydropyridin-1-yl]methyl-1H-pyrrolo[2,3-b]pyridine;

3-(4-phenoxymethyl-1,2,3,6-tetrahydropyridin-1-yl)methyl-1H-pyrrolo[2,3-b]pyridine;

(E)-3-[4-(2-(5-methylfuran-2-yl)ethenyl)-1,2,3,6-tetrahydropyridin-1-yl]methyl-1H-pyrrolo[2,3-b]pyridine;

3-(6-phenyl-1,2,3,4-tetrahydroisoquinolin-2-yl)methyl-1H-pyrrolo[2,3-b]pyridine;

3-(6-methoxy-1,2,3,4-tetrahydroisoquinolin-2-yl)methyl-1H-pyrrolo[2,3-b]pyridine;

3-(7-phenyl-1,2,3,4-tetrahydroisoquinolin-2-yl)methyl-1H-pyrrolo[2,3-b]pyridine;

3-(7-benzyloxy-1,2,3,4-tetrahydroisoquinolin-2-yl)methyl-1H-pyrrolo[2,3-b]pyridine:

3-[7-(thiophen-3-yl)-1,2,3,4-tetrahydroisoquinolin-2-yl]methyl-1H-pyrrolo[2,3-b]pyridine;

3-[6-(4-chlorophenyl)-1,2,3,4-tetrahydroisoquinolin-2-yl]methyl-1H-pyrrolo[2,3-b]pyridine;

3-(5-phenyl-1,2,3,4-tetrahydroisoquinolin-2-yl)methyl-1H-pyrrolo[2,3-b]pyridine;

3-(5-benzyloxy-1,2,3,4-tetrahydroisoquinolin-2-yl)methyl-1H-pyrrolo[2,3-b]pyridine;

3-(5-phenoxy-1,2,3,4-tetrahydroisoquinolin-2-yl)methyl-1H-pyrrolo[2,3-b]pyridine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

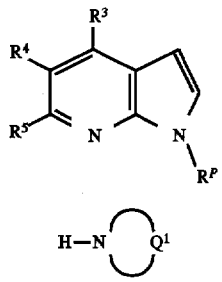

(III)

(IV)

wherein $R^3$, $R^4$ and $R^5$ are as defined above, $Q^1$ represents the residue of a moiety of formula Qa to Qc as defined above, and $R^P$ corresponds to the group R as defined above or represents a suitable protecting group; in the presence of a substantially equimolar amount of formaldehyde; followed, where required, by removal of the protecting group $R^P$; and subsequently, if necessary, N-alkylation by standard methods to introduce the moiety R.

The reaction is conveniently carried out by stirring the reactants in aqueous acetic acid, ideally in the presence of a buffer such as sodium acetate trihydrate, suitably at room temperature.

The formaldehyde may be utilised in the form of paraformaldehyde; or as a solution of formaldehyde in an inert solvent, e.g. 37% aqueous formaldehyde.

The protecting group $R^P$, when present, is suitably an acyl moiety such as acetyl, which can conveniently be removed as necessary by treatment under strongly basic conditions, e.g. sodium methoxide in methanol. Alternatively, the protecting group $R^P$ may be a carbamoyl moiety such as t-butoxycarbonyl (BOC), which can conveniently be removed as necessary by treatment under mildly acidic conditions.

In an alternative procedure, the compounds according to the present invention may be prepared by a process which comprises reacting a compound of formula IV as defined above with a compound of formula V:

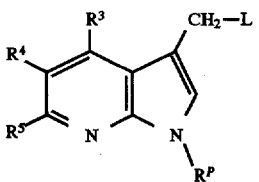

(V)

wherein $R^3$, $R^4$, $R^5$ and $R^P$ are as defined above, and L represents a suitable leaving group; followed, where required, by removal of the protecting group $R^P$; and subsequently, if necessary, N-alkylation by standard methods to introduce the moiety R.

The leaving group L is suitably a halogen atom, e.g. chlorine or bromine; or a dialkylamino group, e.g. dimethylamino.

When L represents a halogen atom, the reaction between compounds IV and V is conveniently carried out by stirring the reactants under basic conditions in a suitable solvent, for example potassium carbonate in N,N-dimethylformamide, or triethylamine in tetrahydrofuran or acetonitrile. Where L represents a dialkylamino group, the reaction is conveniently effected by heating the reactants in an inert solvent such as toluene, typically at the reflux temperature of the solvent.

Where they are not commercially available, the starting materials of formula III, IV and V may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM MgSO$_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM CaCl$_2$, 5 mM MgCl$_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine D$_4$ receptor subtype of below 1.5 µM.

EXAMPLE 1

3-(1,2,3,4-Tetrahydroisoquinoline-2-yl)methyl-1H-pyrrolo[2,3-b]pyridine 1,2,3,4-Tetrahydroisoquinoline (1.37 g, 10.0 mmol) was dissolved in acetic acid (4 ml) and water (2 ml). 37% Aqueous formaldehyde (0.9 ml, 12 mmol) was added and the reaction mixture stirred for five minutes, 1 H-pyrrolo[2,3-b]pyridine (1.18 g, 9.99 mmol) added and the resulting solution stirred at room temperature for 20 h. The reaction mixture was poured into 2M aqueous sodium hydroxide solution (50 ml) and extracted with ethyl acetate (3×50 ml). The combined extracts were washed with water (50 ml) and brine (50 ml). The organic phase was dried (MgSO$_4$) and concentrated in vacuo to give a lemon solid. Recrystallisation from toluene gave the title compound (0.935 g, 36%), as an off-white solid, m.p. 190°–192° C.; (Found: C, 77.51; H, 6.50; N, 15.57. C$_{17}$H$_{17}$N$_3$ requires C, 77.54; H, 6.51; N, 15.96%); δ$_H$ (DMSO-d$_6$) 2.68 (2H, t, J 7.8 Hz, CH$_2$), 2.77 (2H, d, J 7.5 Hz, CH$_2$), 3.55 (2H, s, CH$_2$), 3.79 (2H, s, CH$_2$), 6.97–7.07 (5H, m, ArH), 7.41 (1H, d, J 1.8 Hz, ArH), 8.03 (1H, dd, J 7.8, 1.5 Hz, 4-H), 8.20 (1H, dd, J 4.6, 1.5 Hz, 6-H), and 11.48 (1H, br s, NH); m/z (CI$^+$, NH$_3$) 264 (M+1)$^+$.

Prepared in an analogous manner were:

EXAMPLE 2

3-(4-[2-Phenylethyl]piperidin-1-yl)methyl-1H-pyrrolo[2,3-b]pyridine

M.p. 162°–163° C. (PhMe); (Found: C, 79.29; H, 7.97; N, 12.93. C$_{21}$H$_{25}$N$_3$ requires C, 78.96; H, 7.89; N, 13.15%); δ$_H$ (DMSO-d$_6$) 1.15 (3H, m, 3× piperidinyl H), 1.48 (2H, m, 2× piperidinyl H), 1.64 (2H, m, CH$_2$CH$_2$Ph), 1.85 (2H, t, J 10.2 Hz, 2× piperidinyl H), 2.56 (2H, t, J 8 Hz, CH$_2$CH$_2$Ph), 2.83 (2H, d, J 11.2 Hz, 2× piperidinyl H), 3.57 (2H, s, CH$_2$N), 7.02 (1H, dd, J 7.8, 4.6 Hz, 5-H), 7.12–7.17 (3H, m, ArH), 7.23–7.30 (3H, m, ArH), 8.00 (1H, dd, J 7.8, 1.5 Hz, 4-H), 8.80 (1H, dd, J 4.6, 1.5 Hz, 6-H), and 11.39 (1H, br s, NH); m/z (CI$^+$, NH$_3$) 320 (M+1)$^+$.

EXAMPLE 3

3-(4-Phenyl-1,2,3,6-tetrahydropyridin-1-yl)methyl-1H-pyrrolo[2,3-b]pyridine

M.p. 177°–179° C. (MeOH); (Found: C, 78.60; H, 6.80; N, 14.54. C$_{19}$H$_{19}$N$_3$ requires C, 78.86; H, 6.62; N, 14.52%); δ$_H$ (DMSO-d$_6$) 2.45 (2H, br s, CH$_2$), 2.66 (2H, t, J 5.6 Hz, CH$_2$), 3.09 (2H, d, J 3.2 Hz, CH$_2$), 3.74 (2H, s, CH$_2$N), 6.15 (1H, m, CH), 7.03 (1H, dd, J 7.8, 4.6 Hz, 5-H), 7.19–7.26 (1H, m, ArH), 7.30–7.32 (2H, m, ArH), 7.38–7.41 (3H, m, ArH), 8.03 (1H, dd, J 7.8, 1.5 Hz, 4-H), 8.19 (1H, dd, J 4.6, 1.5 Hz, 6-H), and 11.46 (1H, br s, NH); m/z (CI$^+$, NH$_3$) 290 (M+1)$^+$.

EXAMPLE 4

(E)-3-(4-[2-Phenylethenyl]-1,2,3,6-tetrahydropyridin-1-yl)methyl-1H-pyrrolo[2,3-b]pyridine A solution of (E)-4-(2-phenylethenyl)-1,2,3,6-tetrahydropyridine (204 mg, 1.1 mmol) and 3-dimethylaminomethyl-1H-pyrrolo[2,3-b]pyridine (192 mg, 1.1 mmol) [prepared by the method of M. M. Robison and B. L. Robison, *J. Am. Chem. Soc.*, 1955, 77, 457] in toluene (15 ml) was stirred under reflux for 24 h. The hot solution was filtered and the filtrate allowed to cool, giving the title compound (196 mg, 55%) as a pale brown solid, m.p. 210°–212° C.; (Found: C, 80.43; H, 6.45; N, 13.18. C$_{21}$H$_{21}$N$_3$O. 0.1 PhMe requires: C, 80.31; H, 6.74; N, 12.95%); δ$_H$ (CDCl$_3$) 2.42 (2H, br s, 3'-CH$_2$), 2.72–2.75 (2H, m, 2'-CH$_2$), 3.20 (2H, br s, 6'-CH$_2$), 3.83 (2H, s, CH$_2$N), 5.82 (1H, br s, CH=CR), 6.44 (1H, d, J 16.1 Hz, CH=CHPh), 6.78 (1H, d, J 16.3 Hz, CH=C HPh), 7.07–7.10 (1H, m, 5-H), 7.17–7.21 (1H, m, ArH), 7.26–7.31 (3H, m, ArH), 7.38–7.40 (2H, m, ArH), 8.09 (1H, dd, J 7.9, 1.5 Hz, 4-H), 8.31 (1H, dd, J 4.8, 1.5 Hz, 4-H), and 9.31 (1H, br s, NH); m/z (CI$^+$, NH$_3$) 316 (M+1)$^+$.

EXAMPLE 5

3-(4-Phenylethyl-1,2,3,6-tetrahydropyridin-1-yl)methyl-1H-pyrrolo[2,3-]pyridine M.p. 121°–122° C. (MeOH); (Found: C, 79.06; H, 7.28; N, 13.27. C$_{21}$H$_{23}$N$_3$ requires C, 79.46; H, 7.30; N, 13.24%); δ$_H$ (DMSO-d$_6$) 2.02 (2H, br s, tetrahydropyridinyl CH$_2$), 2.19 (2H, t, J 7.8 Hz, CH$_2$CH$_2$Ph) 2.49–2.52 (2H, m, CH$_2$), 2.65 (2H, t, J 8.0 Hz, CH$_2$), 2.85 (2H, s, CH$_2$), 3.65 (2H, s, NCH$_2$Ar), 5.34 (1H, s, CH=CR), 7.02 (1H, dd, J 7.8, 4.6 Hz, 5-H), 7.13–7.19 (3H, m, ArH), 7.23–7.27 (2H, m, ArH), 7.33 (1H, d, J 2.2 Hz, 2-H), 7.99 (1H, dd, J 7.8, 1.3 Hz, 4-H), 8.18 (1H, dd, J 4.6, 1.5 Hz, 6-H), and 11.42 (1H, br s, NH); m/z (CI$^+$, NH$_3$) 318 (M+1)$^+$.

EXAMPLE 6

3-(4-Naphthalen-2-yl-1,2,3,6-tetrahydropyridin-1-yl)methyl-1H-pyrrolo[2,3-b]pyridine

Step 1

1-(4-Hydroxy-4-naphthalen-2-yl-piperidin-1-yl)ethanone

2-Bromonaphthalene (24.75 g, 0.12 mol) in tetrahydrofuran (180 ml) was slowly added to magnesium (2.9 g, 0.12 mol) in tetrahydrofuran (20 ml) and the mixture stirred at room temperature for one hour. The resultant solution was slowly added to 1-acetyl-4-piperidone (16.9 g, 0.12 mol) in tetrahydrofuran (200 ml) at −78° C., and then allowed to stir to room temperature. The white suspension formed was hydrolysed with hydrochloric acid (120 ml, 1M) and the organic layer removed and concentrated in vacuo. The residue was taken up in dichloromethane, dried (MgSO$_4$), and concentrated to leave a clear oil. Trituration of this oil with diethyl ether gave 1-(4-hydroxy-4-naphthalen-2-yl-piperidin-1-yl)ethanone (13.92 g, 43%) as a white solid; δ$_H$ (CDCl$_3$) 1.90 (4H, m, 2× piperidinyl CH$_2$), 2.10 (2H, m, piperidinyl CH$_2$), 2.15 (3H, s, COCH$_3$), 3.20 (1H, m, piperidinyl H), 3.70 (1H, m, piperidinyl H), 4.60 (1H, br m, OH), 7.50 (2H, m, ArH), 7.60 (1H, dd, J 9.6, 1.6 Hz, ArH), and 7.90 (4H, m, ArH).

Step 2

4-Naphthalen-2-yl-1,2,3,6-tetrahydropyridine 1-(4-Hydroxy-4-naphthalen-2-yl-piperidin-1-yl)ethanone (3.40 g, 13 mmol) was dissolved in hydrochloric acid (50 ml, 6M) and the solution refluxed for 12 hours. The resultant mixture was cooled in ice, basified with sodium hydroxide solution (32 ml, 10M) and extracted with dichloromethane (2×100 ml). The extracts were combined, dried (MgSO$_4$) and concentrated to give 4-naphthalen-2-yl-1,2,3,6-tetrahydropyridine (2.12 g, 78%) as a tan solid; δ$_H$ (CDCl$_3$)

2.60 (2H, m, tetrahydropyridinyl CH$_2$), 3.20 (2H, t, J 5.6 Hz, tetrahydropyridinyl CH$_2$), 3.60 (2H, m, tetrahydropyridinyl CH$_2$), 6.30 (1H, m, CH=CR), 7.45 (2H, m, ArH), 7.60 (1H, dd, J 8.4, 1.4 Hz, ArH), and 7.80 (4H, m, ArH).

Step 3

3-(4-Naphthalen-2-yl-1,2,3,6-tetrahydropyridin-1-yl) methyl-1H-pyrrolo[2,3-b]pyridine 4-Naphthalen-2-yl-1,2,3,6-tetrahydropyridine (597 mg, 2.9 mmol) was reacted with 3-dimethylaminomethyl-1H-pyrrolo[2,3-b]pyridine (500 mg, 2.9 mmol) as exemplified in Example 4 to give the title compound (619 mg, 63%) as tan crystals, m.p. 223°–225° C. (EtOH); (Found: C, 81.05; H, 6.24; N, 12.19. C$_{23}$H$_{21}$N$_3$ requires C, 81.38; H, 6.24; N, 12.38%); δ$_H$ (DMSO-d$_6$) 2.60 (2H, m, tetrahydropyridinyl CH$_2$), 2.72 (2H, t, J 5.7 Hz, tetrahydropyridinyl CH$_2$), 3.16 (2H, d, J 2.7 Hz, tetrahydropyridinyl CH$_2$), 3.78 (2H, s, ArCH$_2$N), 6.34 (1H, m, CH=CR), 7.04 (1H, dd, J 7.5, 1.5 Hz, 5-H), 7.40 (1H, d, J 2.3 Hz, ArH), 7.44 (2H, m, ArH), 7.66 (1H, dd, J 1.6, 7.8 Hz, ArH), 7.86 (4H, m, ArH), 8.06 (1H, d, J 7.5 Hz, 4-H), 8.20 (1H, d, J 1.5 Hz, 6-H, and 11.48 (1H, br s, NH); m/z (CI$^+$, NH$_3$) 340 (M+1)$^+$.

EXAMPLE 7

3-(4-[4-Methoxyphenyl]-1,2,3,6-tetrahydropyridin-1-yl)methyl-1H-pyrrolo[2,3-b]pyridine

Step 1

1-(4-Hydroxy-4-[4-methoxyphenyl]-piperidin-1-yl) ethanone

4-Bromoanisole (22.4 g, 0.12 mol) in tetrahydrofuran (180 ml) was slowly added to magnesium (2.9 g, 0.12 mol) in tetrahydrofuran (20 ml) and the mixture stirred for one hour at room temperature. The solution formed was slowly added to a solution of 1-acetyl-4-piperidone (16.9 g, 0.12 mol) in tetrahydrofuran (200 ml) at −78° C., and the suspension produced was stirred to room temperature for 2 hours. Hydrochloric acid (120 ml, 1M) was added and the organic phase was separated and concentrated in vacuo. The residue was taken up in dichloromethane (300 ml), washed with water (300 ml) and dried (MgSO$_4$). Concentration in vacuo and trituration with diethyl ether gave 1-[4-hydroxy-4-(4-methoxyphenyl)-piperidin-1-yl]ethanone (14.75 g, 50% yield) as a white solid; δ$_H$ (CDCl$_3$) 1.7–2.1 (4H, m, 2× piperidinyl CH$_2$), 2.1 (3H, s, COCH$_3$), 3.1 (1H, m, piperidinyl H), 3.6–3.8 (3H, m, piperidinyl H), 3.8 (3H, s, ArOCH$_3$), 4.6 (1H, m, OH), 6.9 (2H, d, J 10 Hz, ArH), and 7.4 (2H, d, J 10 Hz, ArH).

Step 2

4-(4-Methoxyphenyl)-1,2,3,6-tetrahydropyridine 1-(4-Hydroxy-4-[4-methoxyphenyl]piperidin-1-yl) ethanone (14.75 g, 59 mmol) was dissolved in hydrochloric acid (250 mg, 6M) and refluxed for 12 hours. The reaction mixture was cooled in ice and basified with sodium hydroxide solution (155 ml, 10M), then extracted with dichloromethane (2×500 ml). The extractions were combined, dried (MgSO$_4$), and concentrated in vacuo. The crude product was purified by flash chromatography eluting with 10% methanol in dichloromethane, containing 1% aqueous ammonia. Concentration of the appropriate fractions gave 4-(4-methoxyphenyl)-1,2,3,6-tetrahydropyridine (2.65 g, 24%) as a tan solid; δ$_H$ (DMSO-d$_6$) 2.3 (2H, m, tetrahydropyridinyl CH$_2$), 2.9 (2H, t, J 5.6 Hz, tetrahydropyridinyl CH$_2$), 3.4 (2H, d, J 3.4 Hz, tetrahydropyridinyl CH$_2$), 3.7 (3H, s, ArOCH$_3$), 6.1 (1H, m, CH=CR), 6.9 (2H, d, J 9.6 Hz, ArH), 7.3 (2H, d, J 9.6 Hz, ArH), and 9.6 (1H, br s, NH).

Step 3

3-(4-[4-Methoxyphenyl]-1,2,3,6-tetrahydropyridin-1-yl) methyl-1H-pyrrolo[2,3-b]pyridine 4-(4-Methoxyphenyl)-1,2,3,6-tetrahydropyridine (540 mg, 2.8 mmol) was reacted with 3-dimethylaminomethyl-1H-pyrrolo[2,3-b]pyridine (500 mg, 2.8 mmol) as in Example 4 to give the title compound (367 mg, 41%) as tan crystals, m.p. 202°–204° C. (iPrOH); (Found: C, 73.51; H, 6.74; N, 12.15. C$_{20}$H$_{21}$N$_3$O.0.33 H$_2$O.0.2 C$_3$H$_8$O requires C, 73.34; H, 6.95; N, 12.45%); δ$_H$ (DMSO-d$_6$) 2.44 (2H, m, tetrahydropyridinyl CH$_2$), 2.70 (2H, m, tetrahydropyridinyl CH$_2$), 3.10 (2H, m, tetrahydropyridinyl CH$_2$), 3.74 (3H, s, ArOCH$_3$), 3.76 (2H, s, ArCH$_2$N), 6.04 (1H, m, CH=CR), 6.90 (2H, d, J 8.6 Hz, ArH), 7.04 (1H, dd, J 7.7, 4.6 Hz, 5-H), 7.36 (2H, d, J 8.5 Hz, ArH), 7.40 (1H, s, 2-H), 8.06 (1H, d, J 7.7 Hz, 4-H), 8.20 (1H, d, J 4.6 Hz, 6-H), and 11.48 (1H, br s, NH); m/z (CI$^+$, NH$_3$) 320 (M+1)$^+$.

EXAMPLE 8

3-(4-[1H-Indol-5-yl]-1,2,3,6-tetrahydropyridin-1-yl) methyl-1H-pyrrolo[2,3-b]pyridine

Step 1

5-Bromo-1-triisopropylsilyl-1H-indole

5-Bromoindole (14.04 g, 72 mmol) in tetrahydrofuran (50 ml) was added dropwise to a suspension of sodium hydride (60% dispersion in oil; 3.04 g, 76 mmol) in tetrahydrofuran (100 ml) and the resultant solution stirred for one hour at room temperature. Triisopropylsilyltrifluoromethane sulphonate (23.3 g, 76 mmol) was added slowly and the solution stirred for a further one hour. The reaction mixture was washed with sodium hydrogen carbonate solution, dried (MgSO$_4$), and concentrated. The crude mixture was purified by flash chromatography, with hexane as eluant, to give 5-bromo-1-triisopropylsilyl-1H-indole (20.0 g, 79%) as a clear oil; δ$_H$ (CDCl$_3$) 1.10 (18H, d, J 8.4 Hz, 6× CH$_3$), 2.70 (3H, m, 3×CH), 6.55 (1H, d, J 3.9 Hz, ArH), 7.20 (2H, m, ArH), 7.35 (1H, d, J 8.5 Hz, ArH), and 7.75 (1H, d, J 1.4 Hz, ArH).

Step 2

1-[4-Hydroxy-4-(1-triisopropylsilyl-1H-indol-5-yl) piperidin-1-yl)ethanone

5-Bromo-1-triisopropylsilyl-1H-indole (13.7 g, 38.9 mmol) in tetrahydrofuran (250 ml) at −78° C. was treated with t-butyllithium (45.8 ml, 77.8 mmol, 1.7M solution in pentanes) and stirred at this temperature for 15 minutes. The yellow solution formed was added to 1-acetyl-4-piperidone (5.49 g, 38.9 mmol) in tetrahydrofuran (250 ml) at −78° C., and the mixture allowed to warm to room temperature. Hydrochloric acid (40 ml, 1M) was added and the mixture extracted with ethyl acetate (2×500 ml). The extracts were combined, dried (MgSO$_4$) and concentrated. The crude product was purified by flash chromatography using ethyl acetate as eluant, to give 1-[4-hydroxy-4-(1-triisopropylsilyl-1H-indol-5-yl)piperidin-1-yl]ethanone (3.39 g, 21%) as a white solid; δ$_H$ (DMSO-d$_6$) 1.10 (18H, d, J 7.9 Hz, 6×CH$_3$), 1.70 (3H, m, 3×CH), 2.00 (2H, m, piperidinyl H), 2.05 (3H, s, COCH$_3$), 2.45 (1H, m, piperidinyl H), 3.00 (1H, m, piperidinyl H), 3.30 (1H, m, piperidinyl H), 3.50 (1H, m, piperidinyl H), 3.70 (1H, m, piperidinyl H), 4.30 (1H, m, piperidinyl H), 5.00 (1H, s, OH), 6.60 (1H, d, J 2.8 Hz, ArH), 7.30 (1H, d, J 7.8 Hz, ArH), 7.35 (1H, d, J 2.2 Hz, ArH), 7.50 (1H, d, J 7.9 Hz, ArH), and 7.70 (1H, s, ArH).

Step 3

1-(4-[1-Triisopropylsilyl-1H-indol-5-yl]-1,2,3,6-tetrahydropyridin-1-yl)ethanone 1-(4-Hydroxy-4-[1-triisopropylsilyl-1H-indol-5-yl]-piperidin-1-yl)ethanone (3.11 g, 7.4 mmol) in dichloromethane (100 ml) was treated with pyridinium p-toluenesulfonate (3.8 g, 15.1 mmol) and stirred for 72 hours. The solution was poured into water and extracted with dichloromethane (100 ml). The extractions were dried (MgSO$_4$), concentrated and the crude product purified by flash chromatography using ethyl acetate as eluant, to give 1-(4-[1-triisopropylsilyl-1H-indol-5-yl]-1,2,3,6-tetrahydropyridin-1-yl)-ethanone (1.95 g, 66%) as a white solid; $\delta_H$ (CDCl$_3$) 0.80 (18H, d, J 8.5 Hz, 6×CH$_3$), 1.30 (3H, m, 3×CH), 1.75 (3H, d, J 6.7 Hz, COCH$_3$), 2.30 (2H, m, tetrahydropyridinyl H), 3.25 (1H, t, J 5.6 Hz, tetrahydropyridinyl H), 3.40 (1H, t, J 5.6 Hz, tetrahydropyridinyl H), 3.75 (1H, m, tetrahydropyridyl H), 3.85 (1H, m, tetrahydropyridyl H), 5.60 (1H, m, C$\underline{H}$=CR), 6.20 (1H, d, J 2.2 Hz, ArH), 6.80 (2H, m, ArH), 7.00 (1H, d, J 7.3 Hz, ArH), and 7.20 (1H, m, ArH).

Step 4

5-(1,2,3,6-Tetrahydropyridin-4-yl)-1H-indole 1-(4-[1-Triisopropylsilyl-1H-indol-5-yl]-1,2,3,6-tetrahydro-2H-pyridin-1-yl)ethanone (1.95 g, 4.9 mmol)was dissolved in methanol (70 ml), treated with potassium hydroxide solution (35 ml, 40%), and the mixture heated at 60° C. for 12 hours. The reaction mixture was cooled, extracted with ethyl acetate (2×100 mi), and the extracts were combined, dried (MgSO$_4$), and concentrated. The crude product was purified by flash chromatography on silica, using 10% methanol in dichloromethane containing 1% ammonia as eluant, to give 5-(1,2,3,6-tetrahydropyridin-4-yl)-1H-indole (619 mg, 64%) as a yellow solid; $\delta_H$ (CDCl$_3$) 2.10 (2H, m, tetrahydropyridinyl CH$_2$), 2.60 (2H, m, tetrahydropyridinyl CH$_2$), 3.00 (2H, m, tetrahydropyridinyl CH$_2$), 5.50 (1H, m, C$\underline{H}$=CR), 5.90 (1H, s, ArH), 6.60–7.10 (4H, m, ArH).

Step 5

3-(4-[1H-Indol-5-yl]-1,2,3,6-tetrahydropyridin-1-yl)methyl-1H-pyrrolo[2,3-b]pyridine 5-(1,2,3,6-Tetrahydropyridin-4-yl)-1H-indole (200 mg, 1.0 mmol) and 3-dimethylaminomethyl-1H-pyrrolo[2,3-b]pyridine (177 mg, 1.01 mmol) were coupled as described in Example 4 to give a solid which was purified by flash chromatography, eluting with 10% methanol in dichloromethane containing 1% ammonia. Recrystallisation from methanol gave the title compound (115 mg, 35%) as a tan solid, m.p. 187°–189° C.; (Found: C, 73.78; H, 6.34; N, 16.13. C$_{21}$H$_{20}$N$_4$.0.75 H$_2$O requires C, 73.77; H, 6.34; N, 16.39%); $\delta_H$ (DMSO-d$_6$) 2.68 (2H, m, tetrahydropyridinyl H), 3.10 (2H, s, tetrahydropyridinyl H), 3.18 (1H, d, J 4.4 Hz, tetrahydropyridinyl H), (other tetrahydropyridinyl H obscured by solvent at 3.30), 3.74 (2H, s, ArC$\underline{H}_2$N), 6.02 (1H, m, CH=CR), 6.40 (1H, s, ArH), 7.04 (1H, dd, J 7.5, 3.2 Hz, 5-H), 7.20 (1H, d, J 8.2 Hz, ArH), 7.32 (2H, m, ArH), 7.40 (1H, s, ArH), 7.52 (1H, s, ArH), 8.04 (1H, d, J 7.5 Hz, 4-H), 8.18 (1H, d, J 3.2 Hz, 6-H), 11.00 (1H, br s, NH), and 11.48 (1H, br s, NH); m/z (CI$^+$, NH$_3$) 329 (M+1)$^+$.

EXAMPLE 9

3-(4-Benzofuran-5-yl-1,2,3,6-tetrahydropyridin-1-yl)methyl-1H-pyrrolo[-2,3-pyridine Step 1

5-Bromobenzofuran

A solution of 4-bromophenol (17.3 g, 100 mmol) in dimethylformamide (40 ml) was treated with bromoacetaldehyde dimethyl acetal (16.9 g, 100 mmol) and potassium carbonate (13.8 g, 100 mmol) and heated at 150° C. for 16 h. The mixture was cooled, poured into water (500 ml) and extracted with diethyl ether (3×100 ml). The combined organic extracts were dried (MgSO$_4$), concentrated, and filtered through a plug of silica gel eluting with 10% diethyl ether in hexane. The resulting oil (15 g) was added to a solution of polyphosphoric acid (~12 g) in toluene (100 mL) and heated at 80° C. for 16 h. The mixture was cooled and the toluene layer was decanted off and washed with saturated aqueous sodium hydrogen carbonate, dried (MgSO$_4$), concentrated and the residue distilled to give 5-bromobenzofuran (6 g) as a colourless oil, bp. 98° C./1 mmHg; $\delta_H$ (DMSO-d$_6$) 6.96 (1H, m, ArH), 7.45 (1H, m, ArH), 7.59 (1H, m, ArH), 7.91 (1H, m, ArH), and 8.05 (1H, m, ArH).

Step 2

1-(4-Benzofuran-5-yl-4-hydroxypiperidin-1-yl)ethanone

The Grignard of 5-bromobenzofuran (1.54 g, 7.8 mmol) was prepared from magnesium (209 mg, 8.6 mmol) in tetrahydrofuran (10 ml), initiating the reaction with 1,2-dibromoethane. The Grignard was added to a solution of N-acetyl-4-piperidone (1.21 g, 8.6 mmol) in tetrahydrofuran at −78° C. resulting in a thick precipitate. The mixture was warmed to room temperature, digested with 2M hydrochloric acid (10 ml) and extracted with dichloromethane (3×50 ml). The combined organic extracts were dried (MgSO$_4$), concentrated, and purified by flash chromatography, eluting with ethyl acetate, to give the title product as a colourless oil (750 mg); $\delta_H$ (DMSO-d$_6$) 1.66 (1H, m, piperidinyl H), 1.80 (1H, m, piperidinyl H), 2.03 (1H, m, piperidinyl H), 2.04 (3H, s, CH$_3$CO), 2.95 (1H, m, piperidinyl H), 3.30 (1H, m, piperidinyl H), 3.40 (1H, m, piperidinyl H), 3.70 (1H, m, piperidinyl H), 4.32 (1H, m, piperidinyl H), 5.14 (1H, s, OH), 6.93 (1H, m, ArH), 7.44 (1H, m, ArH), 7.51 (1H, m, ArH), 7.75 (1H, m, ArH), and 7.95 (1H, m, ArH).

Step 3

4-Benzofuran-5-yl-1,2,3,6-tetrahydropyridine

A solution of 1-(4-benzofuran-5-yl-4-hydroxypiperidin-1-yl)ethanone (650 mg, 2.51 mmol) in tetrahydrofuran (10 ml) was treated with 6M HCl (10 mL) and heated at 60° C. for 16 h. The mixture was poured into saturated aqueous sodium hydrogen carbonate (100 ml) and extracted with CH$_2$Cl$_2$ (3×100 ml). The combined organic extracts were dried (MgSO$_4$) and concentrated to give the title product (220 mg) as a semi-solid; $\delta_H$ (DMSO-d$_6$) 1.4–3.7 (6H, 3×CH$_2$), 6.16 (1H, m, C$\underline{H}$=CR), 6.95 (1H, m, ArH), 7.45 (1H, m, ArH), 7.59 (1H, m, ArH), 7.72 (1H, m, ArH), and 7.99 (1H, m, ArH).

Step 4

3-(Benzofuran-5-yl-1,2,3,6-tetrahydropyridin-1-yl)methyl-1H-pyrrolo[2,3-b]pyridine

A suspension of 7-azagramine (180 mg, 1.0 mmol) and 4-benzofuran-5-yl-1,2,3,6-tetrahydropyridine (200 mg, 1.0 mmol) in toluene (5 ml) was heated at 110° C. for 16 h. The resulting hot solution was filtered and allowed to cool. The title compound (180 mg) crystallised and was collected by filtration as a white, crystalline solid, m.p. 168°–70° C.; (Found: C, 75.02; H, 5.81; N, 12.28. $C_{21}H_{19}N_3O \cdot 0.33 H_2O$ requires C, 75.20; H, 5.91; N, 12.53); $\delta_H$ (DMSO-$d_6$) 2.50 (2H, br s, tetrahydropyridinyl $CH_2$, obscured by solvent), 2.69 (2H, br s, $CH_2$), 3.11 (2H, br s, tetrahydropyridinyl $CH_2$), 3.76 (2H, s, ArC$\underline{H}_2$N), 6.12 (1H, br s, C$\underline{H}$=CR), 6.91 (1H, s, ArH), 7.03 (1H, m, ArH), 7.40 (2H, m, ArH), 7.51 (1H, m, ArH), 7.64 (1H, s, ArH), 7.95 (1H, m, ArH), 8.04 (1H, m, ArH), 8.20 (1H, m, ArH), and 11.47 (1H, br s, NH); m/z ($CI^+$, $NH_3$) 330 $(M+H)^+$.

EXAMPLE 10

3-(4-Benzofuran-6-yl-1,2,3,6-tetrahydropyridin-1-yl)methyl-1H-pyrrolo[2,3-b]pyridine

A suspension of 7-azagramine (551 mg, 3.15 mmol) and a 1:1 mixture of 4-benzofuran-6-yl-1,2,3,6-tetrahydropyridine and 4-benzofuran-4-yl-1,2,3,6-tetrahydropyridine (645 mg, 3.24 mmol, produced from 3-bromophenol following the analogous procedure described in Example 9) in toluene (10 ml) was heated at 110° C. for 16 h. The resulting hot solution was filtered and cooled. An isomeric mixture of products crystallised from solution and was collected by filtration as a white crystalline solid. The title compound was isolated pure as its trifluoroacetate salt (60 mg) by preparative reversed phase HPLC ($C_{18}$ column, eluting with 30% MeCN in 1% aqueous trifluoroacetic acid, required product is the faster eluting of the two products), m.p. 161°–163° C. ($Et_2O$); (Found: C, 59.73; H, 4.35; N, 9.13. $C_{21}H_{19}N_3O \cdot CF_3CO_2H \cdot H_2O$ requires C, 59.87; H, 4.81; N, 9.11); $\delta_H$ (DMSO-$d_6$) 2.86 (2H, br s, tetrahydropyridinyl $CH_2$), 3.38 (1H, m, tetrahydropyridinyl H), 3.74 (1H, m, tetrahydropyridinyl H), 3.89 (2 H, br s, tetrahydropyridinyl H), 4.60 (2H, br s, ArC$\underline{H}_2$N), 6.25 (1H, br s, C$\underline{H}$=CR), 6.95 (1H, s, ArH), 7.21 (1H, m, ArH), 7.40 (1H, m, ArH), 7.64 (1H, m, ArH), 7.70 (1H, s, ArH), 7.76 (1H, br s, ArH), 8.00 (1H, br s, ArH), 8.25 (1H, m, ArH), 8.31 (1H, m, ArH), and 9.88 (1H, br s, $NH^+$), and 12.07 (1H, bs, NH); m/z ($CI^+$, $NH_3$) 330 $(M+H)^+$.

EXAMPLE 11

3-(4-Benzothiophen-2-yl]-1,2,3,6-tetrahydropyridin-1-yl)methyl-1H-pyrrolo[2,3-b]pyridine

Step 1

1-Benzyl-4-(benzothiophen-2-yl)-1,2,3,6-tetrahydropyridine

To a solution of benzothiophene (3 g, 22.4 mmol) in anhydrous tetrahydrofuran (50 ml) at −10° C. under nitrogen was added n-butyllithium (9.83 ml of a 2.5M solution in toluene), the mixture was allowed to warm to room temperature and stirred for 1 hr. The reaction mixture was cooled to −40° C. and 1-benzyl-4-piperidone (4.23 g, 22.4 mmol) added, allowed to warm to room temperature and stirred for 14 hr. The reaction mixture was concentrated in vacuo and trifluoroacetic acid (10 ml) added. This mixture was stirred at room temperature for 14 hr and then concentrated in vacuo. The product was extracted into dichloromethane (3×100 ml) from aqueous potassium carbonate. The organic layer was washed with water (1×50 ml), brine (1× 50 ml) and dried ($MgSO_4$). After concentration of the extracts the crude product was purified using silica gel column chromatography to yield the title compound (4.2 g, 68%) as a colourless oil; $\delta_H$ ($CDCl_3$) 2.64 (2H, m, tetrahydropyridinyl $CH_2$), 2.74 (2H, m, tetrahydropyridinyl $CH_2$), 3.18 (2H, m, tetrahydropyridinyl $CH_2$), 3.65 (2H, s, PhC$\underline{H}_2$N), 6.18 (1H, m, C$\underline{H}$=CR), 7.11 (1H, s, 3'-H), and 7.24–7.73 (9H, m, Ar—H).

Step 2

4-(Benzothiophen-2-yl)-1,2,3,6-tetrahydropyridine Hydrochloride

To a solution of 1-benzyl-4-(benzothiophen-2-yl)-1,2,3,6-tetrahydropyridine (4 g, 13.1 mmol) in anhydrous dichloromethane (50 ml) at 0° C. under nitrogen was added 2-chloroethylchloroformate (1.84 ml, 17.0 mmol) and the mixture stirred for 1 hr. The reaction mixture was concentrated in vacuo and methanol (20 ml) added and the solution heated to reflux for 1 hr. After cooling the title compound was collected by filtration (2.2 g, 67%), m.p. 269° C. (dec.).

Step 3

3-(4-(Benzothiophen-2-yl)-1,2,3,6-tetrahydropyridin-1-yl)methyl-1H-pyrrolo[2,3-b]pyridine Reaction of 3-dimethylaminomethyl-1H-pyrrolo[2,3-b]pyridine and 4-(benzothiophen-2-yl)-1,2,3,6-tetrahydropyridine in an analogous manner to Example 4 gave the title compound, m.p. 241°–246° C. (dec.); (Found: C, 72.85; H, 5.54; N, 12.06; $C_{21}H_{19}N_3S$ requires C, 73.01; H, 5.54; N, 12.16%); $\delta_H$ (DMSO-$d_6$) 2.51 (2H, br s, tetrahydropyridinyl $CH_2$), 2.67 (2H, m, tetrahydropyridinyl $CH_2$), 3.14 (2H, m, tetrahydropyridinyl $CH_2$), 3.76 (2H, s, $CH_2N$), 6.19 (1H, br s, C$\underline{H}$=CR), 7.03 (1H, m, ArH), 7.31 (2H, m, 3'-H and ArH), 7.74 (1H, d, J 8 Hz, ArH), 7.86 (1H, d, J 8 Hz, ArH), 8.05 (1H, d, J 8 Hz, ArH), 8.20 (1H, m, ArH), and 11.45 (1H, br s, NH); m/z ($CI^+$, $NH_3$) 346 $(M+1)^+$.

EXAMPLE 12

3-[4-(Benzofuran-2-yl)-1,2,3,6-tetrahydropyridin-1-yl)]methyl-1H-pyrrolo[2,3-b]pyridine

Step 1

4-(Benzofuran-2-yl)-1-benzyl-4-hydroxypiperidine

To a solution of benzofuran (4 g, 33.9 mmol) in tetrahydrofuran (90 ml) at −10° C. was slowly added a solution of n-butyllithium (2.5M in hexanes, 13.6 ml, 34 mmol), keeping the temperature at −10° C. The reaction was stirred and allowed to warm to room temperature over 1 hr, after which a solution of 1-benzyl-4-piperidone (6.3 ml, 34 mmol) in tetrahydrofuran (30 ml) was added dropwise. Stirring was continued for 2 hr at room temperature. The solvent was evaporated and the residue partitioned between saturated aqueous sodium carbonate (75 ml) and ethyl acetate (3×100 ml). The combined organics were dried ($MgSO_4$) and evaporated. The residue was purified by column chromatography, eluting with ethyl acetate, to give 4-(benzofuran-2-yl)-1-benzyl-4-hydroxypyridine (7.5 g, 75%); $\delta_H$ ($CDCl_3$) 1.96–2.00 (2H, m, piperidinyl $CH_2$), 2.21–2.29 (2H, m, piperidinyl $CH_2$), 2.44 (1H, t, J 6.2 Hz, piperidinyl CH), 2.56 (2H, dt, J 11.1, 2.7 Hz, piperidinyl $CH_2$), 2.64–2.68 (3H, m, piperidinyl $CH_2$, OH), 2.73 (1H, t, J 6.2 Hz, piperidinyl CH), 3.55 (2H, s, PhC$\underline{H}_2$N), 6.58 (1H, s, 3'-H), 7.19–7.34 (7H, m, ArH), 7.44 (1H, d, J 7.3 Hz, ArH), and 7.52 (1H, d, J 6.6 Hz, ArH).

Step 2

2-(1-Benzyl-1,2,3,6-tetrahydropyridin-4-yl)benzofuran

A mixture of the preceding alcohol (2 g, 6.5 mmol) and 4-toluenesulfonic acid monohydrate (1.2 g, 6.6 mmol) in toluene (100 ml) was refluxed under Dean and Stark conditions for 2 hrs. The solvent was evaporated, and the residue partitioned between dichloromethane (3×100 ml) and saturated aqueous sodium carbonate (100 ml). The combined organics were dried (MgSO$_4$) and evaporated to yield the title compound (1.2 g, 64%). An analytical sample was recrystallised from ether to give 2-(1-benzyl-1,2,3,4-tetrahydropyridin-4-yl)benzofuran, m.p. 139°–140° C.; (Found: C, 82.40; H, 6.43; N, 4.67. C$_{20}$H$_{19}$NO.0.1H$_2$O requires C, 82.50; H, 6.65; N, 4.81%); $\delta_H$ (CDCl$_3$) 2.55 (2H, br s, tetrahydropyridinyl CH$_2$), 2.74 (2H, t, J 5.7 Hz, tetrahydropyridinyl CH$_2$), 3.24 (2H, br s, tetrahydropyridinyl CH$_2$), 3.67 (2H, s, NCH$_2$Ph), 6.48–6.52 (2H, m, tetrahydropyridinyl 5-CH, 3'-H), 7.14–7.42 (8H, m, ArH), and 7.49 (1H, d, J 7.5 Hz, ArH); m/z (CI$^+$, NH$_3$), 290 (M+1)$^+$.

Step 3

4-(Benzofuran-2-yl)-1,2,3,6-tetrahydropyridine

To a solution of the foregoing tetrahydropyridine (1.1 g, 3.8 mmol) in dichloromethane (50 ml) at 0° C. was added 1-chloroethylchloroformate (493 μl, 4.6 mmol), keeping the temperature below 0° C. The reaction was allowed to warm to room temperature over 1 hr, after which the solvent was evaporated. Methanol (50 ml) was added to the residue and the mixture heated under reflux for 2 hrs. The solvent was removed by evaporation, and the residue chromatographed on silica, eluting with dichloromethane/methanol/ammonia (90:10:1), to yield the title compound as a buff solid (600 mg, 79%); $\delta_H$ (CDCl$_3$) 2.44–2.48 (2H, m, tetrahydropyridinyl CH$_2$), 3.14 (2H, t, J 5.8 Hz, tetrahydropyridinyl CH$_2$), 3.60–3.63 (2H, m, tetrahydropyridinyl CH$_2$), 6.54–6.58 (2H, m, CH=CR, 3'-H), 7.16–7.26 (2H, m, 5'-H, 6'-H), 7.42 (1H, d, J 7.8 Hz, 7'-H), and 7.50 (1H, d, J 7.2 Hz, 4'-H).

Step 4

3-(4-[Benzofuran-2-y]-1,2,3,6-tetrahydropyridin-1-yl)methylpyrrolo]2,3-b]pyridine Prepared from 4-(benzofuran-2-yl)-1,2,3,6-tetrahydropyridine by the method outlined in Example 4; m.p. 202°–204° C. (DMF/MeOH); (Found: C, 76.12; H, 5.78; N, 12.46. C$_{21}$H$_{19}$N$_3$O.0.1H$_2$O requires C, 76.16; H, 5.84; N, 12.69%); $\delta_H$ (DMSO-d$_6$) 2.46 (2H, br s, tetrahydropyridinyl CH$_2$), 2.68 (2H, t, J 5.6 Hz, tetrahydropyridinyl CH$_2$), 3.16 (2H, br s, tetrahydropyridinyl CH$_2$), 3.77 (2H, s, NCH$_2$Ar), 6.44 (1H, br s, tetrahydropyridinyl 5-CH), 6.78 (1H, s, 3'-H), 7.01–7.05 (1H, m, ArH), 7.19–7.27 (2H, m, ArH), 7.40 (1H, s, 2-H), 7.50 (1H, d, J 8.3 Hz, ArH), 7.57 (1H, d, J 8.3 Hz, ArH), 8.04 (1H, dd, 7.8, 1.2 Hz, 4-H), 8.20 (1H, dd, J 4.6, 1.5 Hz, 6-H), and 11.48 (1H, br s, NH); m/z (CI$^+$, NH$_3$) 330 (MH)$^+$.

EXAMPLE 13

3-[4-(Phenylethynyl)-1,2,3,6-tetrahydropyridin-1-yl)methyl-1H-pyrrolo[2,3-b]pyridine;

M.p. 198°–200° C. (MeOH); (Found: C, 80.23; H, 6.01; N, 13.03. C$_{21}$H$_{19}$N$_3$ requires C, 80.48; H, 6.11; N, 13.41%); $\delta_H$ (DMSO-d$_6$) 2.25 (2H, br s, tetrahydropyridinyl CH$_2$), 2.58 (2H, t, J 5.6 Hz, tetrahydropyridinyl CH$_2$), 3.16–3.17 (2H, m, tetrahydropyridinyl CH$_2$), 3.73 (2H, s, NCH$_2$Ar), 6.14 (1H, br s, tetrahydropyridinyl 5-CH), 7.02–7.05 (1H, m, ArH), 7.34–7.42 (6H, m, ArH), 8.02 (1H, d, J 6.5 Hz, ArH), 8.19 (1H, dd, J 4.7, 1.6 Hz, 6-H), and 11.44 (1H, br s, NH); m/z (CI$^+$, NH$_3$) 314 (M+1)$^+$.

EXAMPLE 14

(E)-3-[4-(thiophen-3-yl)ethenyl)-1,2,3,6-tetrahydropyridin-1-yl]methyl-1H-pyrrolo[2,3-b]pyridine M.p. 215–217° C. (MeOH); (Found: C, 71.15; H, 5.92; N, 12.78. C$_{19}$H$_{19}$N$_3$S requires C, 70.99; H, 5.96; N, 13.07%); $\delta_H$ (DMSO-d$_6$) 2.26 (2H, br s, tetrahydropyridinyl CH$_2$), 2.61 (2H, t, J 5.6 Hz, tetrahydropyridinyl CH$_2$), 3.05 (2H, br s, tetrahydropyridinyl CH$_2$), 3.72 (2H, s, NCH$_2$Ar), 5.81 (1H, br s, tetrahydropyridinyl 5-CH), 6.47 (1H, d, J 16.2 Hz, CCH=CH), 6.72 (1H, d, J 16.2 Hz, CH=CHAr), 7.01–7.04 (1H, m, ArH), 7.33–7.37 (2H, m, ArH), 7.42 (1H, br s, ArH), 7.48–7.50 (1H, m, ArH), 8.02 (1H, d, J 6.7 Hz, ArH), and 8.19 (1H, dd, J 4.6, 1.4 Hz, 6-H); m/z (CI$^+$, NH$_3$) 322 (M+1)$^+$, 339 (M+NH$_4$$^+$).

EXAMPLE 15

(E)-3-(4-[2-(2-Chlorophenyl)ethenyl]-1,2,3,6-tetrahydropyridin-1-yl)methylpyrrolo[2,3-b]pyridine M.p. 174°–176° C. (xylene); (Found: C, 71.38; H, 5.62; N, 11.70. C$_{21}$H$_{20}$ClN$_3$.0.2H$_2$O requires C, 71.36; H, 5.82; N, 11.89%); $\delta_H$ (DMSO-d$_6$) 2.31 (2H, br s, tetrahydropyridinyl CH$_2$), 2.64 (2H, br s, tetrahydropyridinyl CH$_2$), 3.08 (2H, br s, tetrahydropyridinyl CH$_2$), 3.74 (2H, s, NCH$_2$Ar), 5.98 (1H, br s, tetrahydropyridinyl 5-CH), 6.70 (1H, d, J 16.1 Hz, CH=CHAr), 6.94 (1H, d, J 16.1 Hz, CH=CHAr), 7.01–7.05 (1H, m, ArH), 7.23–7.32 (2H, m, ArH), 7.37–7.43 (2H, m, ArH), 7.72 (1H, d, J 6.7 Hz, ArH), 8.03 (1H, d, J 7.7 Hz, ArH), 8.19 (1H, br s, ArH), and 11.46 (1H, br s, NH); m/z (CI$^+$, NH$_3$) 350 (M+1)$^+$.

EXAMPLE 16

(E)-3-(4-[2-(4-Chlorophenyl)ethenyl]-1,2,3,6-tetrahydronpyridin-1-yl)methylpyrrolo[2,3-b]pyridine M.p. 214°–217° C. (xylene); (Found: C, 71.34; H, 5.87; N, 11.60. C$_{21}$H$_{20}$ClN$_3$.0.2H$_2$O requires C, 71.36; H, 5.82; N, 11.89%); $\delta_H$ (DMSO-d$_6$) 2.29 (2H, br s, tetrahydropyridinyl CH$_2$), 2.61 (2H, t, J 5.7 Hz, tetrahydropyridinyl CH$_2$), 3.07 (2H, br s, tetrahydropyridinyl CH$_2$), 3.73 (2H, s, NCHAr), 5.91 (1H, br s, tetrahydropyridinyl 5-CH), 6.44 (1H, d, J 16.3 Hz, CH=CHAr), 6.90 (1H, d, J 16.3 Hz, CH=CHAr), 7.01–7.04 (1H, m, ArH), 7.34–7.38 (3H, m, ArH), 7.48 (2H, d, J 8.5 Hz, ArH), 8.02 (1H, d, J 7.8 Hz, ArH), 8.15–8.19 (1H, m, ArH), and 11.45 (1H, bs, NH); m/z CI$^+$, NH$_3$) 350 (M+1)$^+$.

EXAMPLE 17

(E)-3-[4-(2-(thiophen-2-yl)ethenyl)-1,2,3,6-tetrahydropyridin-1-yl]methyl-1H-pyrrolo[2,3-b]pyridine M.p. 202°–204° C. (MeOH); (Found: C, 70.59; H, 5.94; N, 12.20. C$_{19}$H$_{19}$N$_3$S requires C, 70.99; H, 5.96; N, 13.07%); $\delta_H$ (DMSO-d$_6$) 2.26 (2H, br s, tetrahydropyridinyl CH$_2$), 2.60 (2H, t, J 5.7 Hz, tetrahydropyridinyl CH$_2$), 3.05 (2H, br s, tetrahydropyridinyl CH$_2$), 3.72 (2H, s, NCH$_2$Ar), 5.85 (1H, br s, tetrahydropyridinyl 5-H), 6.58 (1H, d, J 16.1 Hz, CH=CHAr), 6.64 (1H, d, J 16.1 Hz, CH=CHAr), 6.98–7.07 (3H, m, ArH), 7.37 (2H, br s, ArH), 8.02 (1H, d, J 6.4 Hz, ArH), 8.19 (1H, d, J 3.1 Hz, ArH), and 11.42 (1H, br s, NH).

EXAMPLE 18

3-(4-[2-(Furan-2-yl)ethyl]-1,2,3,6-tetrahydropyridin-1-yl)methyl-1H-pyrrolo[2,3-b]pyridine

Step 1

1-(Pyridin-4-yl)-2-(furan-2-yl)ethene

A solution of 4-methylpyridine (15 g, 0.16 mol) in acetic anhydride (100 ml) was treated with 2-furaldehyde (15.5 g, 0.16 mol) and heated at reflux for 16 hr. The solvent was evaporated to give a black oil which was treated with water (30 ml) and stirred for 30 mins at room temperature. Ethyl acetate (150 ml) and saturated sodium carbonate (100 ml) were then added and the stirring continued for 30 mins. The supernatant was decanted to leave a black oily residue which was retained (A). From the decanted solvents the organic phase was separated, dried ($Na_2SO_4$) and evaporated to give a black oil (B). The oily residue (A) was dissolved in dichloromethane (150 ml), washed with saturated sodium carbonate solution (100 ml), dried ($Na_2SO_4$) and evaporated to give a black oil which was combined with oil (B). The mixture was chromatographed on silica gel with a gradient of ethyl acetate in hexane (50%–100%) as eluant to afford the title compound as a brown solid (9.8 g, 36%); $δ_H$ (DMSO-$d_6$) 6.58–6.64 (1H, m, furanyl H), 6.66–6.72 (1H, m, furanyl H), 6.96 (1H, d, J 17.5 Hz, ArC$\underline{H}$=CHAr'), 7.42 (1H, d, J 17.5 Hz, ArCH=C$\underline{H}$Ar'), 6.50–6.58 (2H, m, pyridinyl CH), 7.78–7.82 (1H, m, furanyl H), and 8.50–8.51 (2H, m, pyridinyl H).

Step 2

1-(Pyridin-4-yl)-2-(furan-2-yl)ethane

A solution of 1-(pyridin-4-yl)-2-(furan-2-yl)ethene (8 g, 46.8 mmol) in methanol (200 ml) was treated with ammonium formate (14.7 g, 234.0 mmol). 10% Palladium on charcoal catalyst (400 mg, 5% (w/w)) was added and the mixture was stirred at reflux for five hours. The catalyst was filtered off and the solvent evaporated. The residue was partitioned between dichloromethane and water. The organic layer was separated, dried ($MgSO_4$) and evaporated to give a beige oil. This material was chromatographed on silica gel with a gradient of ethyl acetate in hexane (50%–100%) as eluant to afford the title compound as a colourless oil (2.5 g, 31%); $δ_H$ (DMSO-$d_6$) 2.94–3.06 (4H, m, 2×$CH_2$), 6.06–6.12 (1H, m, furanyl H), 6.32–6.38 (1H, m, furanyl H), 7.20–7.28 (2H, m, pyridinyl H), 7.50–7.56 (1H, m, furanyl H), and 8.40–8.50 (2H, m, pyridinyl H).

Step 3

1-Benzyl-4-(2-[furan-2-yl]ethyl)-1,2,3,6-tetrahydropyridine

A solution of 1-(pyridin-4-yl)-2-(furan-2-yl)ethane (2 g, 11.6 mmol) in anhydrous dimethylformamide (5 ml) was treated with benzyl bromide (1.5 ml, 12.7 mmol) and the reaction stirred at room temperature for one hour. The reaction was diluted with ethanol (50 ml), treated with sodium borohydride (0.55 g, 14.5 mmol) and heated at reflux for one hour. The solvent was evaporated and the residue partitioned between ethyl acetate and water. The organic was separated, dried ($Na_2SO_4$) and evaporated to give crude product as a yellow oil. This material was triturated with diethyl ether to afford the title compound (2.3 g, 68%) as a colourless solid; $δ_H$ (DMSO-$d_6$) 1.92–2.10 (2H, m, tetrahydropyridinyl $CH_2$), 2.14–2.30 (2H, m, $CH_2$), 2.36–2.50 (2H, m, $CH_2$), 2.60–2.82 (2H, m, tetrahydropyridinyl $CH_2$), 2.84–2.90 (2H, m, tetrahydropyridinyl $CH_2$), 3.50 (2H, br s, PhC$\underline{H}_2$N), 5.32–5.44 (1H, m, tetrahydropyridinyl 5-H), 6.02–6.10 (1H, m, furanyl H), 6.30–6.36 (1H, m, furanyl H), 7.16–7.36 (5H, m, ArH), and 7.44–7.52 (1H, m, furanyl H); m/z (CI$^+$, $NH_3$) 268 (M+1)$^+$.

Step 4

4-(2-[Furan-2-yl]ethyl)-1,2,3,5-tetrahydropyridine

A cooled (0° C.) solution of 1-benzyl-4-(2-[furan-2-yl]ethyl)-1,2,3,6-tetrahydropyridine (1.8 g, 6.8 mmol) in anhydrous dichloromethane (20 ml) was treated with 1-chloroethylchloroformate (0.95 ml, 8.8 mmol) dropwise. The mixture was stirred for 1 hr at 0° C. The solvent was evaporated and the residue dissolved in methanol (60 ml). This solution was heated at reflux for one hour whereupon the solvent was evaporated. The residue was partitioned between dichloromethane and saturated aqueous potassium carbonate solution. The organic phase was separated, dried ($Na_2SO_4$) and evaporated to give the title compound (867 mg, 72%) as a colourless oil; $δ_H$ (DMSO-$d_6$) 1.84–1.96 (2H, m, tetrahydropyridinyl $CH_2$), 2.16–2.30 (2H, m, $CH_2$), 2.64–2.80 (4H, m, tetrahydropyridinyl $CH_2$ and $CH_2$), 3.06–3.10 (2H, m, tetrahydropyridinyl $CH_2$), 5.40–5.46 (1H, m, tetrahydropyridinyl 5-H), 6.06–6.12 (1H, m, furanyl H), 6.32–6.38 (1H, m, furanyl H), and 7.48–7.56 (1H, m, furanyl H).

Step 5

3-(4-[2-(Furan-2-yl)ethyl]-1,2,3,6-tetrahydropyridin-1-yl)methyl-1H-pyrrolo[2,3-b]pyridine A solution of 4-(2-[furan-2-yl]ethyl)-1,2,3,6-tetrahydropyridine (506 mg, 2.86 mmol) and 3-dimethylaminomethyl-1H-pyrrolo[2,3-b]pyridine (500 mg, 2.86 mmol) in toluene (10 ml) was stirred at reflux for 10 hours. The solvent was evaporated and the residue chromatographed with 3% methanol in dichloromethane as eluant to afford the title compound (200 mg, 23%) as a colourless solid, m.p. 105° C.; (Found: C, 73.84; H, 6.72; N, 13.31. $C_{19}H_{21}N_3O$ requires C, 74.24; H, 6.89; N, 13.67); $δ_H$ (DMSO-$d_6$) 2.00–2.06 (2H, m, tetrahydropyridinyl $CH_2$), 2.22 (2H, t, J 7.7 Hz, $CH_2$), 2.48–2.54 (2H, m, $CH_2$), 2.68 (2H, t, J 7.3 Hz, tetrahydropyridinyl $CH_2$), 2.84–2.89 (2H, m, tetrahydropyridinyl $CH_2$), 3.66 (2H, s, NC$H_2$Ar), 5.34–5.38 (1H, m, tetrahydropyridinyl 5-H), 6.06 (1H, d, J 2.9 Hz, furanyl 3-H), 6.31 (1H, dd, J 3.0, 1.9 Hz, furanyl 4-H), 7.02 (1H, dd, J 7.8, 4.6 Hz, 5-H), 7.32 (1H, d, J 2.3 Hz, furanyl 5-H), 7.46 (1H, d, J 3.0 Hz, 2-H), 7.99 (1H, m, dd, J 7.8, 4.1 Hz, 4-H), 8.18 (1H, dd, J 4.6, 1.4 Hz, 6-H), and 11.38 (1H, br s, NH); m/z (CI$^+$, $NH_3$) 308 (M+1)$^+$.

EXAMPLE 19

3-(4-[2-(Tetrahydrofuran-2-yl)ethyl]-1,2,3,6-tetrahydropyridin-1-yl)methyl-1H-pyrrolo[2,3-b]pyridine

Step 1

4-(2-[Tetrahydrofuran-2-yl]ethyl)pyridine

A solution of 1-(pyridin-4-yl)-2-(furan-2-yl)ethene (15.0 g, 87.7 mmol) [Example 18, Step 1] in methanol (300 ml) was treated with ammonium formate (27.6 g, 438.5 mmol) and 10% palladium on charcoal catalyst (1.5 g, 10% (w/w)). The mixture was stirred at reflux for 3 hours. The catalyst was removed by filtration and the solvent was evaporated in vacuo. The residue was partitioned between dichloromethane and water. The organic phase was separated, dried (MgSO$_4$) and evaporated in vacuo. The residue was chromatographed with 1:1 hexane/ethyl acetate as eluant to afford the title compound as a colourless oil (3.0 g, 19%); δ$_H$ (DMSO-d$_6$) 1.35–1.50 (1H, m, tetrahydrofuranyl H), 1.70–2.00 (5H, m, CH$_2$ and 3×tetrahydrofuranyl H), 2.54–2.76 (2H, m, CH$_2$), 3.54–3.82 (3H, m, tetrahydrofuranyl H), 7.22 (2H, d, J 7.1 Hz, ArH), and 8.46 (2H, d J 7.0 Hz, ArH); m/z (CI$^+$, NH$_3$) 178 (M+1)$^+$.

Step 2

1-Benzyl-4-(2-[tetrahydrofuran-2-yl]ethyl)-1,2,3,6-tetrahydropyridine

A solution of 4-(2-[tetrahydrofuran-2-yl]ethyl)pyridine (3.0 g, 16.9 mmol) in anhydrous dimethylformamide (5 ml) was treated with benzyl bromide (2.2 ml, 18.6 mmol) and the mixture was stirred at room temperature for one hour. The reaction was diluted with absolute ethanol (100 ml), treated with sodium borohydride (0.8 g, 21.2 mmol) and stirred at reflux for one hour. The solvent was evaporated in vacuo and the residue partitioned between diethyl ether and water. The organic layer was separated, dried (Na$_2$SO$_4$) and evaporated in vacuo. The residue was chromatographed with 3% methanol in dichloromethane as eluant to afford the title compound (3.75 g, 82%) as a colourless oil; δ$_H$ (DMSO-d$_6$) 1.30–2.08 (8H, m, 4×CH$_2$), 2.45–2.52 (2H, m, tetrahydropyridinyl CH$_2$), 2.52–2.56 (2H, m, CH$_2$), 2.60–2.66 (2H, m, tetrahydropyridinyl CH$_2$), 3.50 (2H, s, PhCH$_2$N), 3.52–3.80 (3H, m, tetrahydrofuranyl CH$_2$ and CH), 5.50–5.55 (1H, m, tetrahydropyridinyl 5-H), and 7.20–7.34 (5H, m, ArH); m/z (CI$^+$, NH$_3$) 272 (M+1)$^+$.

Step 3-(4-[2-(Tetrahydrofuran-2-yl)ethyl]-1,2,3,6-tetrahydropyridin-1-yl)methyl-1H-pyrrolo[2,3-b]pyridine A solution of the foregoing compound (3.75 g, 13.8 mmol) in anhydrous dichloromethane (150 ml) was cooled to 0° C. and treated with a solution of 1-chloroethylchloroformate (1.94 ml, 18.0 mmol) in anhydrous dichloromethane (50 ml). After stirring at room temperature for one hour, the solvent was evaporated and the residue redissolved in methanol (200 ml). This solution was stirred at reflux for two hours. The solvent was evaporated and the residue partitioned between dichloromethane and saturated aqueous potassium carbonate solution. The organic phase was separated, dried (MgSO$_4$) and evaporated to afford the crude product (2.49 g, 99.6%) as a gummy solid.

A solution of the crude tetrahydropyridine (517 mg, 2.86 mmol) and 3-dimethylaminomethyl-1H-pyrrolo[2,3-b]pyridine (500 mg, 2.86 mmol) in toluene (10 ml) was stirred at reflux for 10 hours. The solvent was evaporated and the residue chromatographed with 3% methanol in dichloromethane as eluant to afford the title compound (175 mg, 20%) as a colourless 25 solid, m.p. 70°–72° C.; (Found: C, 72.29; H, 7.86; N, 13.97. C$_{19}$H$_{25}$N$_3$O.0.25H$_2$O requires C, 72.23; H, 8.13; N, 13.30); δ$_H$ (DMSO-d$_6$) 1.30–1.60 (3H, m, 3×tetrahydrofuranyl H), 1.70–2.08 (7H, m, 1×tetrahydrofuranyl H, CH$_2$CH$_2$ and 1×tetrahydropyridinyl CH$_2$), 2.50 (2H, m, tetrahydropyridinyl CH$_2$ under DMSO peak), 2.86 (2H, br s, tetrahydropyridinyl CH$_2$), 3.50–3.76 (5H, m, ArCH$_2$N and 3×tetrahydrofuranyl H), 5.30–5.36 (1H, m, tetrahydropyridinyl 5-H), 7.02 (1H, dd, J 7.8, 4.6 Hz, 5-H), 7.33 (1H, d, J 2.2 Hz, 2-H), 7.98 (1H, dd, J 7.8, 1.1 Hz, 4-H), 8.18 (1H, dd, J 4.6, 1.1 Hz, 6-H), and 11.42 (1H, m, NH). m/z (CI$^+$, NH$_3$) 312 (M+1)$^+$.

EXAMPLE 20

3-(4-[2-(5-Methylfuran-2-yl)ethyl]-1,2,3,6-tetrahydropyridin-1-yl)methyl-1H-pyrrolo[2,3-pyridine 1-Benzyl-4-(2-[5-methylfuran-2-yl]ethyl)-1,2,3,6-tetrahydropyridine was prepared in the same manner as 1-benzyl-4-[2-furan-2-yl]ethyl)-1,2,3,6-tetrahydropyridine (Example 18).

A solution of 1-benzyl-4-(2-[5-methylfuran-2-yl]ethyl)-1, 2,3,6-tetrahydropyridine (1.5 g, 5.34 mmol) in anhydrous dichloromethane (100 ml) was cooled to 0° C. and treated with a solution of 1-chloroethylchloroformate (0.75 ml, 6.94 mmol) in anhydrous dichloromethane (60 ml). After stirring at room temperature for one hour, the solvent was evaporated and the residue redissolved in methanol (160 ml). This solution was stirred at reflux for two hours. The solvent was evaporated and the residue partitioned between dichloromethane and saturated aqueous potassium carbonate solution. The organic phase was separated, dried (MgSO$_4$) and evaporated to afford the crude product (1.0 g, 99%) as a brown oil.

A solution of the crude tetrahydropyridine (500 mg, 2.6 mmol ) and 3-dimethylaminomethyl-1H-pyrrolo[2,3-b]pyridine (416 mg, 2.38 mmol) in toluene (20 ml) was stirred at reflux for 8 hours. The solvent was evaporated and the residue chromatographed with 3% methanol in dichloromethane as eluant to afford the title compound (160 mg, 21%) as a colourless solid, m.p. 118°–119° C.; (Found: C, 74.04; H, 7.01; N, 12.55. C$_{20}$H$_{23}$N$_3$.O0.175H$_2$O requires C, 74.01; H, 7.25; N, 12.95); δ$_H$ (DMSO-d$_6$) 1.95–2.06 (2H, m, tetrahydropyridinyl CH$_2$), 2.14–2.24 (5H, m, CH$_3$ and C H$_2$CH$_2$), 2.48–2.54 (2H, m, CH$_2$CH$_2$), 2.61 (2H, t, J 7.4 Hz, tetrahydropyridinyl CH$_2$), 2.84–2.93 (2H, m, tetrahydropyridinyl CH$_2$), 3.66 (2H, s, NCH$_2$Ar), 5.35–5.40 (1H, m, tetrahydropyridinyl 5-H), 5.87–5.95 (2H, m, furanyl H), 7.01 (1H, dd, J 7.9, 4.8 Hz, 5H), 7.33 (1H, d, J 2.3 Hz, 2-H), 7.99 (1H, dd, J 7.8, 1.2 Hz, 4-H), 8.17 (1H, dd, J 4.6, 1.4 Hz, 6-H), and 11.41 (1H, br s, NH); m/z (CI$^+$, NH$_3$) 322 (M+1)$^+$.

EXAMPLE 21

3-(4-Ethyl-1,2,3,6-tetrahydropyridin-1-yl)methyl-1H-pyrrolo[2,3-b]pyridine

Step 1

1-Benzyl-4-ethyl-1,2,3,6-tetrahydropyridine

A solution of 4-ethylpyridine (3.0 g, 28 mmol) in anhydrous dimethylformamide (10 ml) was treated with benzyl bromide (3.7 ml, 31 mmol) and the mixture was stirred at room temperature for two hours. The reaction mixture was diluted with absolute ethanol (60 ml), treated with sodium borohydride (1.3 g, 35 mmol) and stirred at reflux for one hour. The solvent was evaporated in vacuo and the residue partitioned between dichloromethane and water. The organic phase was separated, dried (MgSO$_4$) and evaporated in vacuo. The residue was chromatographed with 1:1 hexane/ethyl acetate as eluant to give the title compound (1.92 g, 34% over two steps) as a colourless oil; δ$_H$ (CDCl$_3$) 1.00 (3H, t, J 7.5 Hz, CH$_2$CH$_3$), 1.94–2.12 (4H, m, CH$_2$CH$_3$ and tetrahydropyridinyl CH$_2$), 2.55 (2H, t, J 6.3 Hz, tetrahydropyridinyl CH$_2$), 2.90–3.00 (2H, m, tetrahydropyridinyl CH$_2$), 3.58 (2H, s, PhCH$_2$N), 5.32–5.40 (1H, m, tetrahydropyridinyl 5-H), and 7.20–7.40 (5H, m, ArH); m/z (CI$^+$, NH$_3$) 202 (M+1)$^+$.

Step 2

3-(4-Ethyl-1,2,3,6-tetrahydropyridin-1-yl)-methyl-1H-pyrrolo[2,3-b]pyridine

A solution of 1-benzyl-4-ethyl-1,2,3,6-tetrahydropyridine (1.92 g, 9.6 mmol) in anhydrous dichloromethane (50 ml) was cooled to 0° C. and treated with a solution of 1-chloroethylchloroformate (1.34 ml, 12.4 mmol) in anhydrous dichloromethane (10 ml). After stirring at room temperature for one hour, the solvent was evaporated and the residue redissolved in methanol (50 ml). This solution was heated at reflux for one hour. The solvent was evaporated and the residue partitioned between dichloromethane and saturated aqueous potassium carbonate solution. The organic phase was separated, dried (MgSO$_4$) and evaporated in vacuo to afford the crude product (320 mg, 30%) as a colourless oil. A solution of the crude tetrahydropyridine (320 mg, 2.9 mmol) and 3-dimethylaminomethyl-1H-pyrrolo[2,3-b]pyridine (504 mg, 2.9 mmol) in toluene (10 ml) was stirred at reflux for 16 hours. The solvent was evaporated and the residue chromatographed with 3% methanol in dichloromethane as eluant to afford the title compound (300 mg, 43%) as a colourless solid, m.p. 88°–90° C.; (Found: C, 74.03; H, 7.94; N, 16.97. C$_{15}$H$_{19}$N$_3$.0.125H$_2$O requires C, 73.96; H, 7.97; N, 17.25%); $\delta_H$ (DMSO-d$_6$) 0.99 (3H, t, J 7.5 Hz, CH$_2$CH$_3$), 1.97 (2H, q, J 7.5 Hz, CH$_2$CH$_3$), 2.06–2.12 (2H, m, tetrahydropyridinyl CH$_2$), 2.61 (2H, t, J 5.8 Hz, tetrahydropyridinyl CH$_2$), 3.02–3.08 (2H, m, tetrahydropyridinyl CH$_2$), 3.78 (2H, s, NCH$_2$Ar), 5.34–5.40 (1H, m, tetrahydropyridinyl 5-H), 7.08 (1H, dd, J 7.9, 4.8 Hz, 5-H), 7.29 (1H, m, 2-H), 8.06–8.04 (1H, m, 4-H), 8.28–8.32 (1H, m, 6-H), 9.28 (1H, br s, NH). m/z (CI$^+$, NH$_3$) 242 (M+1)$^+$.

EXAMPLE 22

3-(4-benzoyloxymethyl-1,2,3,6-tetrahydropyridin-1-yl)methyl-1H-pyrrolo[2,3]pyridine.

Step 1

1-Benzyl-4-hydroxymethyl-1,2,3,6-tetrahydropyridine

A solution of 4-hydroxymethylpyridine (20 g, 0.183 mol) in anhydrous dimethylformamide (70 ml) was treated with benzyl bromide (24 ml, 0.202 mol) and the mixture was stirred at 100° C. for two hours. The reaction was cooled to room temperature and diluted with absolute ethanol (250 ml). Sodium borohydride (8.7 g, 0.229 mol) was added portionwise and the mixture stirred at reflux for 3 hours. The solvent was evaporated in vacuo and the residue partitioned between dichloromethane and water. The organic phase was separated, dried (MgSO$_4$) and evaporated in vacuo. The residue was chromatographed with 1:1 hexane/ethyl acetate as eluant to the title compound (13 g, 35%) as a lemon yellow solid; $\delta_H$ (CDCl$_3$) 2.12–2.20 (2H, m, tetrahydropyridinyl CH$_2$), 2.60 (2H, t, J 7.5 Hz, tetrahydropyridinyl CH$_2$), 2.96–3.04 (2H, m, tetrahydropyridyl CH$_2$), 3.60 (2H, s, PhCH$_2$N), 4.00–4.04 (2H, m, CH$_2$OH), 5.60–5.66 (1H, m, tetrahydropyridinyl 5-H), and 7.20–7.40 (5H, m, ArH). m/z (CI$^+$, NH$_3$) 204 (M+1)$^+$.

Step 2

Benzoic acid 1-benzyl-1,2,3,6-tetrahydropyridin-4-ylmethyl ester

A cooled (ice-bath) solution of the foregoing compound (1 g, 4.9 mmol) in dichloromethane (30 ml) was treated with sodium hydroxide solution (2M, 30 ml) and a solution of benzoylchloride (0.58 ml, 4.9 mmol) in dichloromethane (10 ml). The mixture was stirred at 0° C. for 2 hours. The organic layer was separated, dried (MgSO$_4$) and evaporated in vacuo to afford the title compound (1.37 g, 91%) as a colourless oil; $\delta_H$ (DMSO-d$_6$) 2.12–2.20 (2H, m, tetrahydropyridinyl CH$_2$), 2.55 (2H, t, J 7.5 Hz, tetrahydropyridinyl CH$_2$), 2.95–3.05 (2H, m, tetrahydropyridinyl CH$_2$), 3.55 (2H, s, PhCH$_2$N), 4.72 (2H, s, CH$_2$O), 5.75–5.82 (1H, m, tetrahydropyridinyl 5-H), 7.22–7.38 (5H, m, ArH), 7.48–7.57 (2H, m, ArH), 7.64–7.70 (1H, m, ArH), and 7.96–8.04 (2H, m, ArH); m/z (CI$^+$, NH$_3$) 308 (M+1)$^+$.

Step 3

3-(4-benzoyloxymethyl-1,2,3,6-tetrahydropyridin-1-yl)methyl-1H-pyrrolo[2,3]pyridine A solution of benzoic acid 1-benzyl-1,2,3,6-tetrahydropyridin-4-ylmethyl ester (1.35 g, 4.4 mmol) in anhydrous dichloromethane (50 ml) was cooled to 0° C. and treated with a solution of 1-chloroethyl-chloroformate (0.62 ml, 5.7 mmol) in anhydrous dichloromethane (10 ml). After stirring at 0° C. for 1.5 hours, the solvent was evaporated and the residue redissolved in methanol (50 ml). This solution was stirred at reflux for two hours. The solvent was evaporated and the residue partitioned between ethyl acetate and saturated aqueous potassium carbonate solution. The organic phase was separated, dried (MgSO$_4$) and evaporated in vacuo to afford the crude product (520 mg, 58% over two steps) as a colourless oil. A solution of the crude tetrahydropyridine (520 mg, 2.5 mmol) and 3-dimethylaminomethyl-1H-pyrrolo[2,3-b]pyridine (520 mg, 2.5 mmol) in toluene (20 ml) was stirred at reflux for 9 hours. The solvent was evaporated and the residue chromatographed with 5% methanol in dichloromethane as eluant to afford the title compound (480 mg, 55%) as a colourless solid, m.p. 126° C.; (Found: C, 72.42; H, 6.08; N, 12.15. C$_{21}$H$_{21}$N$_3$O$_2$ requires C, 72.60; H, 6.09; N, 12.10%); $\delta_H$ (CDCl$_3$) 2.20–2.30 (2H, m, tetrahydropyridinyl CH$_2$), 2.68 (2H, t, J 5.7 Hz, tetrahydropyridinyl CH$_2$), 3.05–3.10 (2H, m, tetrahydropyridinyl CH$_2$), 3.80 (2H, s, NCH$_2$Ar), 5.86–5.94 (1H, m, tetrahydropyridinyl 5-H), 4.74 (2H, s, CH$_2$O), 7.07 (1H, dd, J 7.8, 4.7 Hz, 5-H), 7.20–7.30 (1H, m, ArH), 7.38–7.45 (2H, m, ArH), 7.50–7.60 (1H, m, ArH), 8.00–8.10 (3H, m, ArH), 8.30 (1H, dd, J 4.7, 1.5 Hz, 6-H), and 9.33 (1H, s, NH); m/z (CI$^+$, NH$_3$) 348 (M+1)$^+$.

EXAMPLE 23

(E)-3-(4-[2-(3-Methoxyphenyl)ethenyl]-1,2,3,6-tetrahydropyridin-1-yl)methyl-1H-pyrrolo[2,3-b]pyridine M.p. 186°–188° C. (PhMe); (Found: C, 76.52; H, 6.93; N, 11.55. C$_{22}$H$_{23}$N$_3$O requires C, 76.49; H, 6.71; N, 12.16%); $\delta_H$ (CDCl$_3$) 2.44 (2H, br s, tetrahydropyridinyl CH$_2$), 2.77 (2H, br s, tetrahydropyridinyl CH$_2$), 3.23 (2H, br s, tetrahydropyridinyl CH$_2$), 3.81 (3H, s, OCH$_3$), 3.86 (2H, s, ArCH$_2$N), 5.81 (1H, br s, tetrahydropyridinyl 5-H), 6.41 (1H, d, J 16.0 Hz, ArCH=CHR), 6.75–6.79 (1H, m, 4'-H), 6.77 (1H, d, J 16.0 Hz, ArCH=CHR), 6.93 (1H, br s, 2'-H), 6.99 (1H, d, J 7.7 Hz, 6'-H), 7.08 (1H, dd, J 7.9, 4.8 Hz, 5-H), 7.22 (1H, t, J 7.9 Hz, 5'-H), 7.33 (1H, br s, 2-H), 8.09 (1H, d, J 7.9 Hz, 4-H), 8.31 (1H, dd, J 4.8, 1.6 Hz, 6-H), and 9.15 (1H, br s, NH); m/z (CI$^+$, NH$_3$) 346 (M+1)$^+$.

EXAMPLE 24

3-(4-Phenoxymethyl-1,2,3,6-tetrahydropyridin-1-yl)methyl-1H-pyrrolo[2,3-b]pyridine M.p. 161°–163° C. (MeOH); (Found: C, 75.05; H, 6.61; N, 12.91. C$_{20}$H$_{21}$N$_3$O requires C, 75.21; H, 6.63; N, 13.16%); $\delta_H$ (CDCl$_3$) 2.25 (2H, br s, tetrahydropyridinyl CH$_2$), 2.69 (2H, t, J 5.7 Hz, tetrahydropyridinyl CH$_2$), 3.09(2H, br s, tetrahydropyridinyl CH$_2$), 3.81 (2H, s, ArCH$_2$N), 4.40 (2H, s, ArCH$_2$O), 5.77 (1H, br s, CH=CR), 6.89–6.95 (3H, m, ArH), 7.08 (1H, dd, J 7.8, 4.7 Hz, 5-H), 7.24–7.29 (3H, m, ArH), 8.07 (1H, dd, J 7.9, 1.5 Hz, 4-H), 8.31 (1H, dd, J 4.8, 1.6 Hz, 6-H), and 9.69 (1H, br s, NH); m/z (CI$^+$, NH$_3$) 320 (M+1)$^+$.

EXAMPLE 25

(E)-3-(4-[2-(5-Methylfuran-2-yl)ethenyl]-1,2,3,6-tetrahydropyridin-1-yl)methyl-1H-pyrrolo[2,3-b]pyridine

Step 1

(E)-1-tert-Butyloxycarbonyl-3-(4-[2-(5-methylfuran-2-yl)ethenyl]-1,2,3,6-tetrahydropyridin-1-yl)methylpyrrolo[2,3-b]pyridine A solution of 1-(5-methylfuran-2-yl)-2-(pyridin-4-yl)ethene (315 mg, 1.7 mmol) in anhydrous dimethylformamide (5 ml) was treated with a solution of (E)-1-tert-butyloxycarbonyl-3-chloromethylpyrrolo[2,3-b]pyridine (500 mg, 1.9 mmol) [prepared using the method of Sanchez-Obregon et al., Can. J. Chem., 1992, 70, 1531–1536] in anhydrous dimethylformamide (5 ml). The mixture was stirred at 70° C. for 16 hours. The reaction was diluted with ethanol (50 ml) and treated with sodium borohydride (81 mg, 2.13 mmol). The mixture was stirred at room temperature for a further two hours whereupon the solvent was evaporated in vacuo and the residue partitioned between ethyl acetate and saturated brine solution. The organic layer was separated, dried (Na$_2$SO$_4$) and evaporated in vacuo. The residue was chromatographed on silica gel with 50% hexane/ethyl acetate as eluant to afford the title compound as an orange oil (160 mg, 22%); $\delta_H$ (CDCl$_3$) 1.60 (9H, s, C(CH$_3$)$_3$), 2.20–2.33 (5H, m, tetrahydropyridinyl CH$_2$ and ArCH$_3$), 2.58–2.66 (2H, m, tetrahydropyridinyl CH$_2$), 3.06–3.16 (2H, m, tetrahydropyridinyl CH$_2$), 3.67 (2H, 2, NCH$_2$Ar), 5.67–5.75 (1H, m, tetrahydropyridinyl 5-H), 5.87–5.91 (1H, m, furan 4-H), 6.04–6.07 (1H, m, furan 3-H), 6.13 (1H, d, J 16.2 Hz, CH=CHAr), 6.58 (1H, d, J 16.1 Hz, CH=CHAr), 7.08–7.14 (1H, m, 5-H), 7.48–7.52 (1H, m, 2-H), 7.96–8.04 (1H, m, 4-H), and 8.40–8.46 (1H, m, 6-H); m/z (CI$^+$, NH$_3$) 420 (M+1)$^+$.

Step 2

(E)-3-(4-[2-(5-methylfuran-2-yl)ethenyl]-1,2,3,6-tetrahydropyridin-1-yl)methyl-1H-pyrrolo[2,3-b]pyridine A solution of (E)-1-tert-butyloxycarbonyl-3-(4-[2-(5-methylfuran-2-yl)ethenyl]-1,2,3,6-tetrahydropyridin-1-yl)methylpyrrolo[2,3-b]pyridine (160 mg, 0.38 mmol) in anhydrous dichloromethane (5 ml) was treated with trifluoroacetic acid (500 ml, 6.5 mmol) and stirred at room temperature for two hours. Ammonium hydroxide solution (5 ml) was added and the whole mixture evaporated in vacuo. The residue was azeotroped with toluene. The crude material was chromatographed on silica gel with 5% methanol in dichloromethane as eluant to afford the title compound as a pale lemon solid (70 mg, 57%), m.p. 180° C. (dec.); (Found: C, 71.47; H, 6.46; N, 12.01. C$_{20}$H$_{21}$N$_3$O.H$_2$O requires C, 71.19; H, 6.87; N, 12.42%); $\delta_H$ (DMSO-d$_6$) 2.15–2.30 (5H, m, tetrahydropyridinyl CH$_2$ and ArCH$_3$), 2.59 (2H, t, J 5.5 Hz, tetrahydropyridinyl CH$_2$), 3.02–3.10 (2H, m, tetrahydropyridinyl CH$_2$), 3.71 (2H, s, NCH$_2$Ar), 5.78–5.86 (1H, m, tetrahydropyridinyl 5-H), 6.05–6.10 (1H, m, furan 4-H), 6.16–6.30 (2H, m, CH=CHAr and furan 3-H), 6.55 (1H, d, J 16.1 Hz, CH=CHAr), 7.02 (1H, dd, J 7.8, 4.8 Hz, 5-H), 7.34–7.38 (1H, m, 2-H), 8.01 (1H, d, J 7.8 Hz, 4-H), 8.18 (1H, d, J 4.6 Hz, 6-H), and 11.45 (1H, s, NH); m/z (CI$^+$, NH$_3$) 320 (M+1)$^+$.

EXAMPLE 26

3-(6-phenyl-1,2,3,4-tetrahydroisoquinolin-2-yl)methyl-1H-pyrrolo[2,3-b]pyridine

A mixture of 6-phenyl-1,2,3,4-tetrahydroisoquinoline (prepared by the method of L. N. Pridgen, J. Heterocyclic Chem. 1980, 17, 1289) (0.5 g, 2.38 mmol) and 3-dimethylaminomethyl-1H-pyrrolo[2,3-b]pyridine (0.4 g, 2.28 mmol) in toluene (5 ml) was heated at reflux under nitrogen for 18 h. The mixture was allowed to cool and the crystallised product collected. Recrystallisation from ethyl acetate afforded the title compound (0.13 g, 17%), m.p. 211°–213° C.; (Found: C, 80.15; H, 6.30; N, 12.32. C$_{23}$H$_{21}$N$_3$.0.3H$_2$O requires C, 80.11; H, 6.31; N, 12.18%); $\delta_H$ (DMSO-d$_6$) 2.73 (2H, br s, CH$_2$CH$_2$Ph), 2.87 (2H, br s, NCH$_2$CH$_2$), 3.61 (2H, s, ArCH$_2$N), 3.83 (2H, s, NCH$_2$Ph), 7.02 (1H, dd, J 7.8, 4.6 Hz, 5-H), 7.18 (1H, d, J 3.2 Hz, 2-H), 7.30–7.45 (6H, m, ArH), 7.60 (2H, d, J 7.6 Hz, ArH), 8.05 (1H, d, J 7.6 Hz, 4-H), 8.20 (1H, dd, J 6.1, 1.4 Hz, 6-H), and 11.48 (1H, br s, NH); m/z (CI$^+$, NH$_3$) 340 (M+1)$^+$.

EXAMPLE 27

3-(6-methoxy-1,2,3,4-tetrahydroisoquinolin-2-yl)methyl-1H-pyrrolo[2,3-b]pyridine A mixture of 6-methoxy-1,2,3,4-tetrahydroisoquinoline (prepared by the method of Helfer, Helv. Chim. Acta, 1924, 7, 945) (0.55 g, 3.36 mmol) and 3-dimethylaminomethyl-1H-pyrrolo[2,3-b]pyridine (0.59 g, 3.36 mmol) in toluene (3 ml) was heated at reflux under nitrogen for 18 h. The mixture was allowed to cool and the crystallised product collected. Recrystallisation from toluene afforded the title compound (0.31 g, 32%), m.p. 144°–146° C.; (Found: C, 73.04; H, 6.43; N, 14.10. C$_{18}$H$_{19}$N$_3$O.0.1H$_2$O requires C, 73.24; H, 6.55; N, 14.23%); $\delta_H$ (DMSO-d$_6$) 2.67 (2H, br s, CH$_2$), 2.76 (2H, t, J 5.4 Hz, CH$_2$), 3.49 (2H, s, CH$_2$), 3.69 (3H, s, OCH$_3$), 3.78 (2H, s, CH$_2$), 6.65 (2H, m, ArH), 6.89 (1H, d, J 9 Hz, ArH), 7.01 (1H, dd, J 7.9, 4.7 Hz, 5-H), 7.40 (1H, d, J 2.2 Hz, ArH), 8.03 (1H, dd, J 7.7, 1.3 Hz, 4-H), 8.19 (1H, dd, J 4.6, 1.4 Hz, 6-H), and 11.47 (1H, br s, NH); m/z (CI$^+$, NH$_3$) 294 (M+1)$^+$.

EXAMPLE 28

3-(7-phenyl-1,2,3,4-tetrahydroisoquinolin-2-yl)methyl-1H-pyrrolo[2,3-b]pyridine

Step 1

7-Phenylisoquinoline

To a slurry of 7-(trifluoromethanesulfonyloxy)isoquinoline (prepared by the method of D. F. Ortwine et al., J. Med. Chem., 1992, 35, 1345) (2.1 g, 7.5 mmol) in toluene (20 ml) was added phenyl boronic acid (1.21 g, 10 mmol) and a 2M solution of sodium carbonate (15 ml). The reaction vessel was filled with nitrogen, tetrakis(triphenylphosphine)palladium(0) (0.25 g, 0.22 mmol) was added and the reaction mixture was heated at 90° C. for 18 h. The reaction mixture was diluted with ethyl acetate (50 ml) and washed with sodium carbonate solution (50 ml). The aqueous solution was extracted with ethyl acetate (2×50 ml). The ethyl acetate extracts were combined, dried over magnesium sulphate, filtered and evaporated under reduced pressure to give an oil. The oil was purified by flash chromatography using hexane/ethyl acetate (1:1) as eluant to give the title compound (1.27 g, 83%); $\delta_H$ (DMSO-$d_6$) 7.41–7.88 (6H, m, ArH and isoquinolinyl H), 7.95 (1H, d, J 6.2 Hz, isoquinolinyl H), 8.14 (1H, dd, J 8.5, 1.75 Hz, isoquinolinyl H), 8.44 (1H, t, J 0.85 Hz, isoquinolinyl H), 8.52 (1H, d, 5.75 Hz, 3-H), and 9.31 (1H, s, 1-H); m/z (CI$^+$, NH$_3$) 206 (M+1)$^+$.

Step 2

7-Phenyl-1,2,3,4-tetrahydroisoquinoline

To a solution of 7-phenylisoquinoline (1.25 g, 6.1 mmol) in methanol (50 ml) was added conc HCl (2 ml) and platinum oxide (100 mg). The reaction mixture was hydrogenated at 50 psi until no further uptake of hydrogen was observed. The catalyst was filtered off, washed with methanol. The filtrate was evaporated under reduced pressure to give a solid. The solid was partitioned between ethyl acetate and sodium carbonate solution. The aqueous solution was extracted with ethyl acetate (2×100 ml). The ethyl acetate extracts were combined, washed with brine (2×100 ml), dried over magnesium sulphate, filtered and evaporated under reduced pressure to give an oil, which crystallised on standing. The solid was a mixture of the title compound and 7-phenyl-decahydroisoquinoline; Rf 0.66 (EtOAc/MeOH/NH$_3$ 5:1:1).

Step 3

7-Phenyl-2-(1H-pyrrolo[2,3-b]pyridin-3-ylmethyl)-1,2,3,4-tetrahydroisoquinoline

The mixture obtained from the previous step (0.5 g, 2.38 mmol) and 3-dimethylaminomethyl-1H-pyrrolo[2,3-b]pyridine (0.42 g, 2.39 mmol) in toluene (3 ml) was heated at reflux under nitrogen for 24 h. The mixture was allowed to cool and the crystalline product collected. The solid was purified by flash chromatography, eluting with dichloromethane/methanol/ammonia. The appropriate fractions were combined to give a solid (0.54 g). The solid was recrystallised from toluene, and purified by reverse phase HPLC on a KR100, 5 μm C$_8$ column (250 mm×20 mm id) using 40% acetonitrile, 60% H$_2$O (containing 0.1% TFA) as eluant. The appropriate fraction was evaporated under reduced pressure to dryness. The residue was partitioned between dichloromethane/methanol (9:1) and sodium hydroxide solution. The organic phase was evaporated under reduced pressure to give a solid. The solid was recrystallised from toluene to give the title compound (0.14 g, 17%), m.p. 203°–205° C.; (Found: C, 79.92; H, 6.02; N, 12.10. C$_{23}$H$_{21}$N$_3$.0.35H$_2$O requires C, 79.90; H, 6.33; N, 12.15%); $\delta_H$ (DMSO-$d_6$) 2.72 (2H, t, J 5.4 Hz, CH$_2$), 2.82 (2H, t, J 5.4 Hz, CH$_2$), 3.63 (2H, s, CH$_2$), 3.82 (2H, s, CH$_2$), 7.02 (1H, dd, J 7.6, 4.7 Hz, 5-H), 7.16 (1H, d, J 7.9 Hz, ArH), 7.29–7.43 (6H, m, ArH), 7.59 (2H, dd, J 6.8, 1.4 Hz, ArH), 8.05 (1H, d, J 7.9 Hz, 4-H), 8.20 (1H, dd, J 4.7, 1.4 Hz, 6-H), and 11.49 (1H, br s, NH); m/z (CI$^+$, NH$_3$) 340 (M+1)$^+$.

EXAMPLE 29

3-(7-benzyloxy-1,2,3,4-tetrahydroisoquinolin-2-yl)methyl-1H-pyrrolo[2,3-b]pyridine Step 1

7-Benzyloxyisoquinoline

To a solution of 7-hydroxyisoquinoline (prepared by the method of R. B. Woodward and W. D. Doering, *J. Am. Chem. Soc.*, 1945, 67, 860) (1.45 g, 10 mmol) in DMF (20 ml) was added sodium hydride (60% dispersion in oil, 0.4 g, 10 mmol) portionwise. After stirring for 30 minutes, benzyl bromide (1.2 ml, 10 mmol) was added and the reaction mixture stirred for 2 h. The reaction mixture was poured into water and extracted with diethyl ether (3×100ml). The ether extracts were combined, washed with 2N sodium hydroxide solution (2×50 ml), brine (50 ml), dried over magnesium sulphate, filtered and evaporated under reduced pressure to give the title compound (1.6 g, 68%); $\delta_H$ (CDCl$_3$) 5.21 (2H, s, OCH$_2$), 7.30–7.51 (7H, m, ArH), 7.59 (1H, d, J 8.3 Hz, ArH), 7.75 (1H, d, J 13 Hz, ArH), 8.42 (1H, d, J 8 Hz, ArH), and 9.14 (1H, s, ArH).

Step 2

7-Benzyloxy-1,2,3,4-tetrahydroisoquinoline

7-Benzyloxyisoquinoline (1.5 g, 6.37 mmol) in methanol (100 ml) was hydrogenated at 50 psi on a Parr apparatus using platinum oxide (100 mg) as catalyst. The catalyst was collected by filtration, the filtrate evaporated under reduced pressure to give an oil which crystallised on treatment with hexane/diethyl ether to give the title compound (0.96 g, 64%); $\delta_H$ (CDCl$_3$) 2.72 (2H, t, J 6 Hz, CH$_2$), 3.11 (2H, t, J 6 Hz, CH$_2$), 3.90 (2H, s, CH$_2$), 6.62 (1H, d, J 2.25 Hz, tetrahydroisoquinolinyl H), 6.78 (1H, dd, J 5.75, 2.75 Hz, tetrahydroisoquinolinyl H), 6.99 (1H, d, J 9.25 Hz, tetrahydroisoquinolinyl H), and 7.25–7.43 (5H, m, ArH).

Step 3

7-Benzyloxy-2-(1H-pyrrolo[2,3-b]pyridin-3-ylmethyl)-1,2,3,4-tetrahydroisoquinoline A mixture of 7-benzyloxy-1,2,3,4-tetrahydroisoquinoline (0.48 g, 2 mmol) and 3-dimethylaminomethyl-1H-pyrrolo[2,3-b]pyridine (0.35 g, 2 mmol) in toluene (5 ml) was heated at reflux under nitrogen for 18 h. The mixture was allowed to cool and the crystallised product collected. The product was purified by flash chromatography using dichloromethane/methanol (10:1) as eluant. The appropriate fractions were combined and evaporated to give a solid. Recrystallisation from toluene afforded the title compound (0.24 g, 32%) m.p. 180°–182° C.; (Found: C, 77.73; H, 6.00; N, 11.11. C$_{24}$H$_{23}$N$_3$O requires C, 78.02; H, 6.27; N, 11.37%); $\delta_H$ (DMSO-$d_6$) 2.68 (4H, m, 2×CH$_2$), 3.51 (2H, s, CH$_2$), 3.78 (2H, s, CH$_2$), 5.01 (2H, s, OCH$_2$), 6.66 (1H, d, J 2.4 Hz, ArH), 6.74 (1H, dd, J 8.3, 2.6 Hz, ArH), 7.02 (2H, m, ArH), 7.32–7.42 (6H, m, ArH), 8.03 (1H, dd, J 7.9, 1.2Hz, 4-H), 8.18 (1H, dd, J 4.7, 1.5 Hz, 6-H), and 11.47 (1H, br s, NH); m/z (CI$^+$, NH$_3$) 370 (M+1)$^+$.

EXAMPLE 30

3-[7-(thiophen-3-yl)-1,2,3,4-tetrahydroisoquinolin-2-]methyl-1H-pyrrolo[2,3-b]pyridine Step 1

7-(3-Thienyl)isoquinoline

Using the method described in Example 28, Step 1 and 3-thiophene boronic acid (1 g, 8 mmol) the title compound was obtained (0.7 g, 54%); $\delta_H$ (CDCl$_3$) 7.47 (1H, dd, J 5.1, 2.9 Hz, thiophene 5-H), 7.53 (1H, dd, J 5.1, 1.3 Hz, thiophene 4-H), 7.61 (1H, dd, J 2.9, 1.3 Hz, thiophene 2-H), 7.64 (1H, d, J 5.7 Hz, isoquinolinyl H), 7.85 (1H, d, J 8.5 Hz, isoquinolinyl H), 7.96 (1H, m, isoquinolinyl H), 8.14 (1H, s, isoquinolinyl H), 8.52 (1H, d, J 5.7 Hz, isoquinolinyl 3-H), and 9.28 (1H, s, isoquinolinyl 1-H); m/z (CI$^+$, NH$_3$) 212 (M+1)$^+$.

Step 2

2-(1H-Pyrrolo[2,3-b]pyridin-3-ylmethyl)-7-thiophen-3-yl-1,2,3,4-tetrahydroisoquinoline A solution of 7-(3-thienyl)isoquinoline (0.15 g, 3 mmol) in dichloromethane was treated with an excess of HCl gas. The mixture was evaporated under reduced pressure to give a colourless solid. The solid was dissolved in ethanol, platinum oxide (100 mg) added, the reaction mixture hydrogenated at 50 psi on a Parr apparatus until uptake of hydrogen ceased. The catalyst was collected by filtration and the filtrate was hydrogenated again using fresh catalyst until the starting material had been consumed. The filtrate was evaporated under reduced pressure. The residue was dissolved in ethyl acetate (100 ml), washed with sodium carbonate solution (100 ml), dried over magnesium sulphate, filtered and evaporated under reduced pressure to give crude 7-(3-thienyl)-1,2,3,4-tetrahydroisoquinoline as an oil (0.41 g, 62%). A mixture of this oil (0.40 g, 1.85 mmol) and 3-dimethylaminomethyl-1H-pyrrolo[2,3-b]pyridine (0.325 g, 1.85 mmol) in toluene (3 ml) was heated at reflux under nitrogen for 6 h. The mixture was allowed to cool and the crystallised product collected. Recrystallisation from toluene afforded the title compound (0.17 g, 28%), m.p. 228°–230° C.; (Found: C, 72.82; H, 5.46; N, 12.05. $C_{21}H_{19}N_3S$ requires C, 73.01; H, 5.54; N, 12.16%); $\delta_H$ (DMSO-$d_6$) 2.72 (2H, t, J 5.4 Hz, $CH_2$), 2.80 (2H, t, J 5 Hz, $CH_2$), 3.59 (2H, s, $CH_2$), 3.82 (2H, s, $CH_2$), 7.02 (1H, dd, J 7.7, 4.7 Hz, 5-H), 7.11 (1H, d, J 8.0 Hz, ArH), 7.35 (1H, s, ArH), 7.42–7.50 (3H, m, ArH), 7.57 (1H, dd, J 5.1, 3 Hz, ArH), 7.76 (1H, s, ArH), 8.04 (1H, dd, J 7.7, 1 Hz, 4-H), 8.20 (1H, dd, J 4.6, 1 Hz, 6-H), and 11.49 (1H, br s, NH); m/z ($CI^+$, $NH_3$) 345 $(M+1)^+$.

EXAMPLE 31

3-[6-(4-chlorophenyl)-1,2,3,4-tetrahydroisoquinolin-2-yl]methyl-1H-pyrrolo[2,3-]pyridine

Step 1

6-Hydroxy-3,4-dihydro-1H-isoquinoline-2-carboxylic acid tert-butyl ester

To a slurry of 6-hydroxy-1,2,3,4-tetrahydroisoquinoline hydrobromide (prepared by the method of Grimewald, J. Med. Chem., 1987, 30, 2208) (1.2 g, 5.2 mmol) and triethylamine (0.8 ml, 5.7 mmol) in dichloromethane (40 ml) was added a solution of di-tert-butyl dicarbonate (1.2 g, 5.5 mmol) in dichloromethane (10 ml). The mixture was stirred for 2 h. The reaction mixture was washed with a solution of citric acid (2×50 ml), brine (2×50 ml), dried over magnesium sulphate, filtered and evaporated under reduced pressure to give the title compound as an oil (1.3 g, 100%); $\delta_H$ ($CDCl_3$) 1.44 (9H, s, $C(CH_3)_3$), 2.77 (2H, t, J 6 Hz, $CH_2$), 3.79 (2H, br s, $CH_2$), 4.54 (2H, s, $CH_2$), 6.64 (1H, s, ArH), 6.69 (1H, d, J 7.5 Hz, ArH), and 6.96 (1H, d, J 8.5 Hz, ArH).

Step 2

6-Trifluoromethanesulfonyloxy-3,4-dihydro-1H-isoquinoline-2-carboxylic acid tert-butyl ester To a solution of 6-hydroxy-3,4-dihydro-1H-isoquinoline-2-carboxylic acid tert-butyl ester (1.3 g, 5.2 mM) and diisopropyethylamine (1 ml) in methanol (40 ml) at 0° C. was added a solution of N-phenyltrifluoromethanesulfonimide (2.14 g, 6 mmol). On completion of the addition the reaction mixture was allowed to warm to room temperature and stirred overnight. A further equivalent of diisopropylethylamine (1 ml) was added, the reaction mixture cooled to 0° C. then a solution of N-phenyltrifluoromethanesulfonimide (2.14 g, 6 mmol) was added and the reaction mixture stirred at room temperature for a further 18 h. The solvent was evaporated under reduced pressure and the residue purified by flash chromatography using hexane/ethyl acetate (4:1) as eluant. The title compound was obtained as an oil, which was taken on crude to the next step without further purification.

Step 3

6-(4-Chlorophenyl)-3,4-dihydro-1H-isoquinoline-2-carboxylic acid tert-butyl ester To a mixture of 6-trifluoromethanesulfonyloxy-3,4-dihydro-1H-isoquinoline-2-carboxylic acid tert-butyl ester (2 g, 5.25 mmol) and 4-chlorophenyl boronic acid (1.17 g, 7.5 mmol)in toluene (20 ml) was added a 2M sodium carbonate solution (7.5 ml). The reaction mixture was stirred under a nitrogen atmosphere, then tetrakis (triphenylphosphine)palladium(0) (0.29 g, 0.25 mmol) was added and the reaction mixture was heated at 90° C. for 18 h. After allowing to cool the reaction mixture was diluted with water (100 ml) and extracted with ethyl acetate (3×100 ml). The ethyl acetate extracts were combined, dried over magnesium sulphate, filtered and evaporated under reduced pressure to give an oil. Purification by flash chromatography using hexane/ethyl acetate as eluant gave the title compound as an oil (0.7 g, 39%); $\delta_H$($CDCl_3$) 1.5 (9H, s, $C(CH_3)_3$), 2.89 (2H, t, J 8.3 Hz, $CH_2$), 3.68 (2H, t, J 8.3 Hz, $CH_2$), 4.61 (2H, s, $CH_2$), and 7.15–7.5 (7H, m, ArH).

Step 4

6-(4-Chlorophenyl)-1,2,3,4-tetrahydroisoquinoline

To a solution of 6-(4-chlorophenyl)-3,4-dihydro-1H-isoquinoline-2-carboxylic acid tert-butyl ester (0.5 g, 1.45 mmol) in dichloromethane (6 ml) was added trifluoroacetic acid (3 ml). The reaction mixture was stirred at room temperature for 1 h. The solvent was evaporated under reduced pressure and the residue partitioned between dichloromethane (3×20 ml) and 1N sodium hydroxide solution (30 ml). The combined organic phases were dried over potassium carbonate, filtered and evaporated under reduced pressure to give an oil. The oil was purified by flash chromatography using dichloromethane/methanol/ammonia 95:5:1 as eluant to afford the title compound as a solid (0.27 g, 76%); $\delta_H$ ($CDCl_3$) 2.9 (2H, t, $CH_2$), 3.24 (2H, t, $CH_2$), 4.1 (2H, s, $CH_2$), and 7.04–7.55 (7H, m, ArH).

Step 5

6-(4-Chlorophenyl)-2-(1H-pyrrolo[2,3-b]pyridin-3-ylmethyl)-1,2,3,4-tetrahydroisoauinoline A mixture of 6-(4-chlorophenyl)-1,2,3,4-tetrahydroisoquinoline (0.23 g, 0.94 mmol) and 3-dimethylaminomethyl-1H-pyrrolo[2,3-b]pyridine (0.168 g, 0.96 mmol) in toluene (15 ml) was heated at reflux under nitrogen for 18 h. The mixture was allowed to cool and the crystallised product collected. Trituration with ethanol gave the title compound (0.18 g, 48%), m.p. 202°–204° C.; (Found: C, 73.02; H, 5.20; N, 11.04. $C_{23}H_{20}ClN_3 \cdot 0.2H_2O$ requires C, 73.18; H, 5.45; N, 11.18%); $\delta_H$ ($CDCl_3$) 2.83 (2H, t, J 5.5 Hz, $CH_2$), 2.94 (2H, t, J 5.5 Hz, $CH_2$), 3.73 (2H, s, $CH_2$), 3.91 (2H, s, $CH_2$), 7.04–7.10 (2H, m, ArH), 7.29–7.50 (7H, m, ArH), 8.12 (7H, dd, J 7.8, 1.5 Hz, 4-H), 8.32 (1H, dd, J 4.75, 1.5 Hz, 6-H), and 9.60 (1H, br s, NH); m/z ($CI^+$, $NH_3$) 374 $(M+1)^+$.

EXAMPLE 32

3-(5-phenyl-1,2,3,4-tetrahydroisoquinolin-2-yl) methyl-1-H-pyrrolo[2,3-b]pyridine Using the procedure described for Example 26 replacing 6-phenyl-1,2,3,4-tetrahydroisoquinoline with 5-phenyl-1,2,3,4-tetrahydroisoquinoline (prepared by the method of L. N. Pridgen, *J. Heterocyclic Chem.*, 1980, 17, 1289) the title compound was obtained as a colourless solid, m.p. 202°–204° C. (toluene); (Found: C, 81.05; H, 6.31; N, 11.90. $C_{23}H_{21}N_3.0.1C_7H_8.0.1H_2O$ requires C, 81.23; H, 6.33; N, 11.99%); $\delta_H$ (DMSO-$d_6$) 2.69 (4H, br s, NCH$_2$CH$_2$Ar), 3.45 (2H, s, ArCH$_2$N), 3.78 (2H, s, ArCH$_2$N), 5.08 (2H, s, ArCH$_2$O), 6.60 (1H, d, J 8 Hz, 6'-H), 6.81 (1H, d, J 8 Hz, 8'-H), 6.95–7.05 (2H, m, ArH), 7.3–7.5 (6H, m, ArH), 8.02 (1H, d, J 8 Hz, 4-H), 8.20 (1H, br s, 6-H), and 11.5 (1H, br s, NH); m/z (CI$^+$, NH$_3$) 340 (M+1)$^+$.

EXAMPLE 33

3-(5-benzyloxy-2,3,4-tetrahydroisoquinolin-2-yl) methyl-1-H-pyrrolo[2,3-b]pyridine Following the procedure for the preparation of Example 29, replacing 7-hydroxyisoquinoline in Step 1 with commercially available 5-hydroxyisoquinoline, afforded the title compound as a colourless solid, m.p. 179°–181° C. (MeOH/EtOH); (Found: C, 77.54; H, 6.19; N, 11.09. $C_{24}H_{23}N_3O.0.1H_2O$ requires C, 77.54; H, 6.19; N, 11.09%); $\delta_H$ (DMSO-$d_6$) 2.69 (4H, br s, NCH$_2$CH$_2$Ar), 3.45 (2H, s, ArCH$_2$N), 3.78 (2H, s, ArCH$_2$N), 5.08 (2H, s, ArCH$_2$O), 6.60 (1H, d, J 8 Hz, 6'-H), 6.81 (1H, d, J 8 Hz, 8'-H), 6.95–7.05 (2H, m, ArH), 7.3–7.5 (6H, m, ArH), 8.02 (1H, d, J 8 Hz, 4-H), 8.20 (1H, br s, 6-H), and 11.5 (1H, br s, NH); m/z (CI$^+$, NH$_3$) 370 (M+1)$^+$.

EXAMPLE 34

3-(5-phenoxy-1,2,3,4-tetrahydroisoquinolin-2-yl) methyl-1-H-pyrrolo[2,3-b]pyridine

Step 1

5-Phenylisoquinoline

Cupric oxide (0.2 g) was added in one portion to a mixture of phenol (2 g, 21 mmol), potassium carbonate (2.7 g, 20 mmol), and 5-bromoisoquinoline (2.1 g, 10 mmol) in pyridine (20 ml) heated at 90° C. under nitrogen. The mixture was then heated at 140° C. for 18 h. After this time the pyridine was removed in vacuo, the residue suspended in ether and the mixture filtered through a pad of silica gel. The solvent was evaporated and the residue purified by column chromatography on silica with ethyl acetate/hexane (1:3–1:1) as eluant to give the title compound as a colourless solid (1.1 g, 49%); $\delta_H$ (CDCl$_3$) 7.1–7.5 (7H, m, ArH), 7.75 (1H, d, J 8 Hz, ArH), 8.02 (1H, d, J 8 Hz, ArH), 8.57 (1H, d, J 8 Hz, ArH); and 9.3 (1H, s, 1-H).

Step 2

5-Phenoxy-1,2,3,4-tetrahydroisoquinoline

A solution of 5-phenoxyisoquinoline (1 g, 4.5 mmol) in methanol (50 ml) was shaken on a Parr hydrogenator at 55 psi hydrogen in the presence of platinum oxide (0.2 g) for 3 h. The catalyst was then removed by filtration and the solvent evaporated. The residue was triturated with hexane to give the title compound as a colourless solid (0.6 g, 60%); $\delta_H$ (CDCl$_3$) 2.65–2.75 (2H, m, ArCH$_2$CH$_2$N), 3.1–3.2 (2H, m, ArCH$_2$CH$_2$N), 4.05 (2H, br s, ArCH$_2$N), 6.75 (1H, d, J 8 Hz, ArH), 6.83 (1H, d, J 8 Hz, ArH), and 6.9–7.35 (6H, m, ArH); m/z (CI$^+$, NH$_3$) 226 (M+1)$^+$.

Step 3

5-Phenoxy-2-(1H-pyrrolo[2,3-b]pyridin-3-ylmethyl)-1,2,3,4-tetrahydroisoquinoline Following the procedure described for Example 26 replacing 6-phenyl-1,2,3,4-tetrahydroisoquinoline with 5-phenoxy-1,2,3,4-tetrahydroisoquinoline the title compound was obtained as a colourless solid, m.p. 179°–180° C. (EtOH/MeOH); (Found: C, 77.55; H, 5.96; N, 11.68. $C_{23}H_{20}N_3O$ requires C, 77.94; H, 5.69; N, 11.86%); $\delta_H$ (CDCl$_3$) 2.8 (4H, m, ArCH$_2$CH$_2$N), 3.71 (2H, s, ArCH$_2$N), 3.89 (2H, s, ArCH$_2$N), 6.72 (1H, d, J 8 Hz, ArH), 6.83 (1H, d, J 8 Hz, ArH), 6.9–7.35 (8H, m, ArH), 8.1 (1H, dd, J 8, 1.5 Hz, 4-H), 8.3 (1H, dd, J 4.5, 1.5 Hz, 6-H), and 10.1 (1H, br s, NH).

We claim:

1. A compound of formula I, or a pharmaceutically acceptable salt thereof:

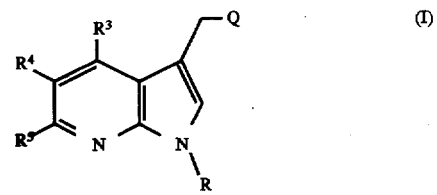

wherein

R represents hydrogen or $C_{1-6}$ alkyl;

Q represents a moiety of formula Qa, Qb or Qc:

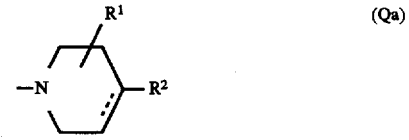

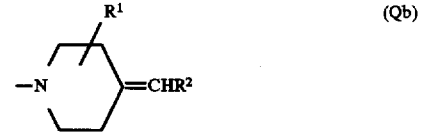

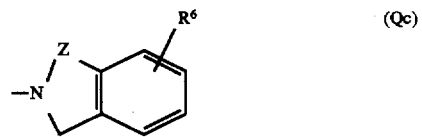

in which the broken line represents an optional chemical bond;

$R^1$ represents hydrogen, or an unsubstituted or substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$) alkenyl or heteroaryl($C_{2-6}$)alkynyl group; wherein aryl is selected from the group consisting of: phenyl and naphthyl; heterocycloalkyl is selected from the group consisting of: azetidinyl, pyrrolidyl, piperidyl, piperazinyl, morpholinyl and tetrahydrofuryl; heteroaryl is selected from the group consisting of: pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl; wherein the substituents are selected from the group consisting of: $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyloxy, $-NR^{v}R^{w}$, $-NR^{v}COR^{w}$, $-NR^{v}CO_{2}R^{w}$, $-NR^{v}SO_{2}R^{w}$, $-CH_{2}NR^{v}SO_{2}R^{w}$, $-NHCONR^{v}R^{w}$, $-PO(OR^{v})(OR^{w})$, $-CONR^{v}R^{w}$, $-SO_{2}NR^{v}R^{w}$ and $-CH_{2}SO_{2}NR^{v}R^{w}$, in which $R^{v}$ and $R^{w}$ independently represent hydrogen, $C_{1-6}$ alkyl, aryl or aryl($C_{1-6}$)alkyl;

$R^2$ represents an unsubstituted or substituted $C_{1-6}$ alkoxy, $C_{2-6}$ alkenyl, $C_{2-6}$ alkynyl, aryl, aryl($C_{1-6}$)alkyl, aryloxy($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group, wherein aryl, heteroaryl, heterocycloalkyl and the substituents are defined above;

$R^3$, $R^4$ and $R^5$ independently represent hydrogen, hydrocarbon, selected from the group consisting of: $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl; a heterocyclic group, selected from the group consisting of: $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups; halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^aR^b$;

Z represents $-CH_2-$ or $-CH_2CH_2-$;

$R^6$ represents hydrogen or halogen, or an unsubstituted or substituted $C_{1-6}$ alkyl, $C_{1-6}$ alkoxy, aryl, aryloxy, aryl($C_{1-6}$)alkyl, aryl($C_{1-6}$)alkoxy or heteroaryl group; wherein aryl, heteroaryl, heterocycloalkyl and the substituents are defined above; and $R^a$ and $R^b$ independently represent hydrogen, hydrocarbon, as defined above, or a heterocyclic group as defined above.

2. A compound as claimed in claim 1 represented by formula IIA, and pharmaceutically acceptable salts thereof:

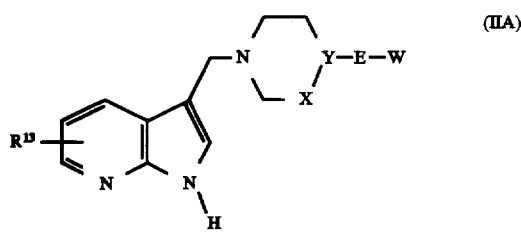

(IIA)

wherein

E represents $-(CH_2)_n-$, $-CH=CH-$ or $-C\equiv C-$;

n is zero, 1, 2 or 3; $-X-Y-$ represents $-CH_2-CH-$ or $-CH=C-$;

W represents a group of formula (i), (ii), (iii), (iv), (v) or (vi):

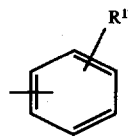 (i)

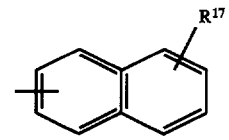 (ii)

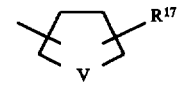 (iii)

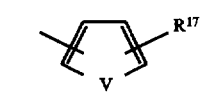 (iv)

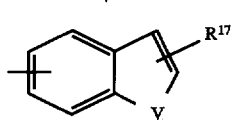 (v)

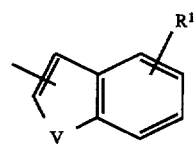 (vi)

in which V represents oxygen, sulphur or NH; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

3. A compound as claimed in claim 2 represented by formula IIB, and salts pharmaceutically acceptable thereof:

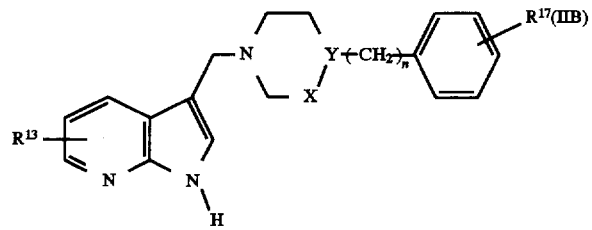

wherein n, X, Y, $R^{13}$ and $R^{17}$ are as defined in claim 2.

4. A compound as claimed in claim 1 represented by formula IIC, and pharmaceutically acceptable salts thereof:

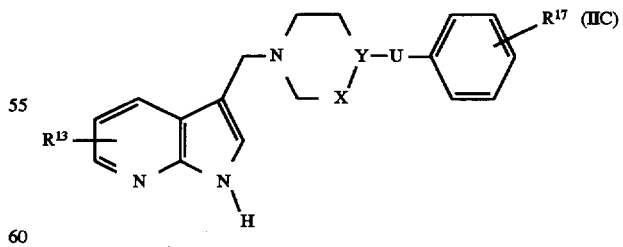

U represents $-CH=CH-$, $-C\equiv C-$ or $-CH_2O-$; and $-X-Y-$ represents $-CH_2-CH-$ or $-CH=C-$; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

5. A compound as claimed in claim 4 wherein U represents —CH=CH—.

6. A compound as claimed in claim 1 represented by formula IID, and pharmaceutically acceptable salts thereof:

(IID)

wherein $R^{13}$ independently represents hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl; and $R^{16}$ represents hydrogen, halogen, $C_{1-6}$ alkyl, $C_{1-6}$ alkoxy, aryl, halo-aryl, aryloxy, aryl($C_{1-6}$)alkyl, aryl($C_{1-6}$) alkoxy or heteroaryl, wherein aryl is selected from the group consisting of: phenyl and naphthyl; heteroaryl is selected from the group consisting of: pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl.

7. A compound as claimed in claim 1 selected from:

3-(1,2,3,4-tetrahydroisoquinolin-2-yl)methyl-1H-pyrrolo[2,3-b]pyridine;

3-[4-(2-phenylethyl)piperidin-1-yl]methyl-1H-pyrrolo[2,3-b]pyridine;

3-(4-phenyl-1,2,3,6-tetrahydropyrid-1-yl)methyl-1H-pyrrolo[2,3-b]pyridine;

(E)-3-[4-(2-phenylethenyl)-1,2,3,6- tetrahydropyrid-1-yl]methyl-1H-pyrrolo[2,3-b]pyridine;

3-[4-(2-phenylethyl)-1,2,3,6-tetrahydropyrid-1-yl]methyl-1H-pyrrolo[2,3-b]pyridine;

3-[4-(naphth-2-yl)-1,2,3,6-tetrahydropyridin-1-yl]methyl-1H-pyrrolo[2,3-b]pyridine;

3-[4-(4-methoxyphenyl)-1,2,3,6-tetrahydropyridin-1-yl]methyl-1H-pyrrolo[2,3-b]pyridine;

3-[4-(1H-indol-5-yl)-1,2,3,6-tetrahydropyridin-1-yl]methyl-1H-pyrrolo[2,3-b]pyridine;

3-[4-(benzofuran-5-yl)-1,2,3,6-tetrahydropyridin-1-yl]methyl-1H-pyrrolo[2,3-b]pyridine;

3-[4-(benzofuran-6-yl)-1,2,3,6-tetrahydropyridin-1-yl]methyl-1H-pyrrolo[2,3-b]pyridine;

3-[4-(benzothiophen-2-yl)-1,2,3,6-tetrahydropyridin-1-yl]methyl-1H-pyrrolo[2,3-b]pyridine;

3-[4-(benzofuran-2-yl)-1,2,3,6-tetrahydropyridin-1-yl]methyl-1H-pyrrolo[2,3-b]pyridine;

3-[4-(2-phenylethynyl)-1,2,3,6-tetrahydropyridin-1-yl]methyl-1H-pyrrolo[2,3-b]pyridine;

(E)-3-[4-(2-(thiophen-3-yl)ethenyl)-1,2,3,6-tetrahydropyridin-1-yl]methyl-1H-pyrrolo2,3-pyridine;

(E)-3-[4-(2-(2-chlorophenyl)ethenyl)-1,2,3,6-tetrahydropyridin-1-yl]methyl-1H-pyrrolo[2,3-b]pyridine;

(E)-3-[4-(2-(4-chlorophenyl)ethenyl)-1,2,3,6-tetrahydropyridin-1-yl]methyl-1H-pyrrolo2,3-b]pyridine;

(E)-3-[4-(2-(thiophen-2-yl)ethenyl)-1,2,3,6-tetrahydropyridin-1-yl]methyl-1H-pyrrolo[2,3-b]pyridine;

3-[4-(2-(furan-2-yl)ethyl)-1,2,3,6-tetrahydropyridin-1-yl]methyl-1H-pyrrolo[2,3-b]pyridine;

3-[4-(2-(tetrahydrofuran-2-yl)ethyl)-1,2,3,6-tetrahydropyridin-1-yl]methyl-1H-pyrrolo[2,3-b]pyridine;

3-[4-(2-(5-methylfuran-2-yl)ethyl)-1,2,3,6-tetrahydropyridin-1-yl]methyl-1H-pyrrolo[2,3-b]pyridine;

3-(4-ethyl-1,2,3,6-tetrahydropyridin1yl)methyl-1H-pyrrolo[2,3-b]pyridine;

3-(4-benzoyloxymethyl-1,2,3,6-tetrahydropyridin-1-yl)methyl-1H-pyrrolo[2,3-b]pyridine;

(E)-3-[4-(2-(3-methoxyphenyl)ethenyl)-1,2,3,6-tetrahydropyridin-1-yl]methyl-1H-pyrrolo[2,3-b]pyridine;

3-(4-phenoxymethyl-1,2,3,6-tetrahydropyridin-1-yl)methyl-1H-pyrrolo[2,3-b]pyridine;

(E)-3-[4-(2-(5-methylfuran-2-yl)ethenyl)-1,2,3,6-tetrahydropyridin-1-yl]methyl-1H-pyrrolo[2,3-b]pyridine;

3-(6-phenyl-1,2,3,4-tetrahydroisoquinolin-2-yl)methyl-1H-pyrrolo[2,3-b]pyridine;

3-(6-methoxy-1,2,3,4-tetrahydroisoquinolin-2-yl)methyl-1H-pyrrolo[2,3-b]pyridine;

3-(7-phenyl-1,2,3,4-tetrahydroisoquinolin-2-yl)methyl-1H-pyrrolo[2,3-b]pyridine;

3-(7-benzyloxy-1,2,3,4-tetrahydroisoquinolin-2-yl)methyl-1H-pyrrolo[2,3-b]pyridine;

3-[7-(thiophen-3-yl)-1,2,3,4-tetrahydroisoquinolin-2-yl]methyl-1H-pyrrolo[2,3-b]pyridine;

3-[6-(4-chlorophenyl)-1,2,3,4-tetrahydroisoquinolin-2-yl]methyl-1H-pyrrolo[2,3-b]pyridine;

3-(5-phenyl-1,2,3,4-tetrahydroisoquinolin-2-yl)methyl-1H-pyrrolo[2,3-b]pyridine;

3-(5-benzyloxy-1,2,3,4-tetrahydroisoquinolin-2-yl)methyl-1H-pyrrolo[2,3-b]pyridine;

3-(5-phenoxy-1,2,3,4-tetrahydroisoquinolin-2-yl)methyl-1H-pyrrolo[2,3-b]pyridine;

and pharmaceutically acceptable salts thereof.

8. A pharmaceutical composition comprising a compound as claimed in claim 1 in association with a pharmaceutically acceptable carrier.

9. A method for the treatment and/or prevention of schizophrenia which method comprises administering to a patient in need of such treatment an effective amount of a compound as claimed in claim 1.

* * * * *